United States Patent
Zhang

(10) Patent No.: US 12,163,127 B2
(45) Date of Patent: Dec. 10, 2024

(54) NON-INVASIVE METHOD AND KIT FOR CAPTURING AND ISOLATING FETAL CELLS FROM MOTHER

(71) Applicant: Jing Zhang, Chongqing (CN)

(72) Inventor: Jing Zhang, Chongqing (CN)

( * ) Notice: Subject to any disclaimer, the term of this patent is extended or adjusted under 35 U.S.C. 154(b) by 1448 days.

(21) Appl. No.: 16/475,319

(22) PCT Filed: Dec. 29, 2017

(86) PCT No.: PCT/CN2017/119951
§ 371 (c)(1),
(2) Date: Jul. 1, 2019

(87) PCT Pub. No.: WO2018/121753
PCT Pub. Date: Jul. 5, 2018

(65) Prior Publication Data
US 2019/0330631 A1    Oct. 31, 2019

(30) Foreign Application Priority Data

Dec. 30, 2016   (CN) .......................... 201611257265.5

(51) Int. Cl.
| | | |
|---|---|---|
| *C12N 15/113* | (2010.01) | |
| *C12N 5/073* | (2010.01) | |
| *C12N 7/00* | (2006.01) | |
| *C12N 15/10* | (2006.01) | |
| *C12N 15/67* | (2006.01) | |
| *G01N 33/49* | (2006.01) | |

(52) U.S. Cl.
CPC .......... *C12N 15/113* (2013.01); *C12N 5/0603* (2013.01); *C12N 7/00* (2013.01); *C12N 15/1037* (2013.01); *C12N 15/1096* (2013.01); *C12N 15/67* (2013.01); *G01N 33/4915* (2013.01); *C12N 2501/599* (2013.01); *C12N 2710/16621* (2013.01); *C12N 2710/16631* (2013.01)

(58) Field of Classification Search
CPC ........ C12N 5/0603; C12N 2710/16621; C12N 2710/16631; C07K 14/005
See application file for complete search history.

(56) References Cited

FOREIGN PATENT DOCUMENTS

| CN | 103205399 A | 7/2013 |
|---|---|---|
| CN | 102220292 B | 8/2014 |
| WO | 2008132753 A2 | 11/2008 |

OTHER PUBLICATIONS

GenBank: AC018398.10 (Year: 2002).*
Xiong, et al., "Angiopoietins and Pregnancy", Journal of International Obstetrics and Gynecology, 36(1), Feb. 28, 2009 (Feb. 28, 2009), ISSN: 1674-1870, pp. 8-14, Feb. 28, 2009 (Feb. 28, 2009).
"*Homo sapiens* angiopoietin-2 (AGPT2) gene, promoter region, 5' UTR and partial cds", GenBank: AY563557.1, NCBI, Sep. 3, 2019.
"Search Report", issued by the Chinese National Intellectual Property Administrations, Peoples Republic of China for Application No. 2016112572655.
"Supplementary Partial European Search Report and Provisional Opinion for EP17886593.7", issued by the European Patent Office, Aug. 7, 2020, pp. 1-15.
Brinch, et al., "Identification of circulating fetal cell markers by microarray analysis", Prenatal Diagnosis, vol. 32, No. 8, May 9, 2012, pp. 742-751.
Budziszewska, et al., "Regulation of the Human Corticotropin-Releasing-Hormone Gene Promoter Activity by Antidepressant Drugs in Neuro-2A and AtT-20 Cells", Neuropsychopharmacology, vol. 29, No. 4, Apr. 1, 2004, pp. 785-794.
Ferraz-De-Souza, et al., "ChIP-on-chip analysis reveals angiopoietin 2 (Ang2, ANGPT2) as a novel target of steroidogenic factor-1 (SF-1, NR5AI) in the human adrenal gland", The FASEB Journal, vol. 25, No. 4, Apr. 1, 2011, pp. 1166-1175.
Hegen, et al., "Expression of Angiopoietin-2 in Endothelial Cells Is Controlled by Positive and Negative Regulatory Promoter Elements", Arteriosclerosis, Thrombosis, and Vascular Biology, vol. 24, No. 10, Oct. 1, 2004, pp. 1803-1809.
Maron, et al., "Gene expression analysis in pregnant women and their infants identifies unique fetal biomarkers that circulate in maternal blood", The Journal of Clinical Investigation, BMJ Group, GB, vol. 117, No. 10, Oct. 1, 2007, pp. 3007-3019.
Zhang, et al., "A novel oHSV-1 targeting telomerase reverse transcriptase-positive cancer cells via tumor-specific promoters regulating the expression of I CP4", Oncotarget, vol. 6, No. 24, May 6, 2015, pp. 20345-20355.
International Search Report and Written Opinion issued by the State Intellectual Property Office of the P.R. of China on Mar. 28, 2018 for PCT/CN2017/119951.
"NCBI Reference Sequence: NG_016619.2" Genbank, Sep. 5, 2016.
Bruno, F.D.S. et al., "ChIP-on-chip analysis reveals angiopoietin 2 (Ang2, ANGPT2) as a novel target of steroidogenic factor-1 (SF-1, NR5A1) in the human adrenal gland", The FASEB Journal, vol. 25, No. 4, ISSN:0892-6638, pp. 1166-1175, Dec. 16, 2010.

* cited by examiner

*Primary Examiner* — Nicole Kinsey White
*Assistant Examiner* — Ruixue Wang
(74) *Attorney, Agent, or Firm* — Jennifer Stachniak; Johnson, Marcou, Isaacs & Nix, LLC

(57) ABSTRACT

Provided are a promoter of a gene specifically expressed in fetal trophoblast cells and a gene specifically expressed in fetal nucleated red blood cell-specific expression gene, as well as a recombinant herpes simplex virus type I obtained by replacing the wild type promoter of the genomic ICP of the recombinant herpes simplex virus type I with the aforesaid promoter and preparation and use thereof. Also provided are a diagnostic kit for prenatal screening and use thereof, as well as a method for isolating fetal cells from a maternal blood sample in pregnancy.

4 Claims, 13 Drawing Sheets

Specification includes a Sequence Listing.

SEQUENCE LISTING

<160> NUMBER OF SEQ ID NOS: 59

<210> SEQ ID NO 1
<211> LENGTH: 1358
<212> TYPE: DNA
<213> ORGANISM: Artificial Sequence
<220> FEATURE:
<223> OTHER INFORMATION: ANGPT2

<400> SEQUENCE: 1

```
ttctgacaca ataaagaagt ttgtgggcca ggcatggtga ctcacacctg taatctcagc      60
actttgggag gccaaaggcg agtcgatcac aaggtcatga gtttgagacc agcctaacat     120
ggtgaaaccc tgtctctact aaaaatacaa aaattagccg ggtgtggtgg cgtttgcctg     180
taatcccagc tgctcaggag cctgaggcaa gagaatcact tgaacccgga aggcggaggt     240
tgcagtgagc caacattgcc ccactgcact ctagcctggt cgacagagcg agactccgtc     300
tcaaaaaaaa aaaaaaaaaa aaaaagtttg tattcctctt tctacacagg cacttaaatt     360
ctaatttctc tattgtaatg taatgaactt aatcagtaca gtgtattttt agagtgaata     420
tccaagtgga gttttttaa agaataaagg tcagagctca gaaactgatg tttctaacgt     480
gacttaataa cagatctttc tatccaactg ttcggaaatg aaaatctttt gtaacttggc     540
tagtggttca agaatcaact aaaatcaatg aatctatttt tccctctgaa aaggcacacg     600
tttacaggag ccaaacttct tcctctttat ttgtaataac aaaaataaac cgaagtcctg     660
acctatttgt aatattttta ttcctaaagg aaaaaacagg aactttcatt gtacttcaac     720
attaaagtta ttacctcaga tattttgcca gcttagcacg gcaaaaatca gtttcagaca     780
aaagagatca actgctctct ctaggaaata cttaattggg gtggtgccta ggaaatgccc     840
aggggtcctg taacagatcg gttttttccca gagggtttct gcagcatggg tcctggttgg     900
agggcaggca ttctgctctg atttttcctg ttgcctggct agtgacccccc tacaggaaga     960
taacggctaa gccaggaggg cggagcagcc cactacacat gtctggctgc tcttatcaac    1020
```

| | |
|---|---:|
| ttatcatata aggaaaggaa agtgattgat tcggatactg acactgtagg atctggggag | 1080 |
| agaggaacaa aggaccgtga aagctgctct gtaaaagctg acacagccct cccaagtgag | 1140 |
| caggactgtt cttcccactg caatctgaca gtttactgca tgcctggaga gaacacagca | 1200 |
| gtaaaaacca ggtttgctac tggaaaaaga ggaaagagaa gactttcatt gacgaccca | 1260 |
| gccatggcag cgtagcagcc ctgcgtttta gacggcagca gctcgggact ctggacgtgt | 1320 |
| gtttgccctc aagtttgcta agctgctggt ttattact | 1358 |

```
<210> SEQ ID NO 2
<211> LENGTH: 2000
<212> TYPE: DNA
<213> ORGANISM: Artificial Sequence
<220> FEATURE:
<223> OTHER INFORMATION: AIF1L

<400> SEQUENCE: 2
```

| | |
|---|---:|
| tggtccctag atgtctgggc agaggtggag aggccgaaga tgggggagct gctgctgcac | 60 |
| agtgagtttg gtgattggcg tctggtgtaa gtgatgtcga gaatatggag ttcttccaag | 120 |
| acctctggga tagggtctga tgtccccctc ccgcctccct ccagtttctc agccgatggc | 180 |
| acacagtcgt cctggtgcct gctcttggca ctcagccttt atccactcaa gccgtgggat | 240 |
| ccagctcagc tcagtcccag catccccgac gggtggagaa ctcgggcctg acatgttgtg | 300 |
| actcacgcag tctgatcatg cctggtgcat gtgctgatct attctctggc cccagaggtg | 360 |
| gggccgctgc cgggtggaat gcggcagctg ttgaacatct ggctagcaat gcagtccagc | 420 |
| agctgagcag aaggtggggt ggcccctgcc ctgtaggatg gctgactgga ccaaccagc | 480 |
| ccaaccggcc agggcaatag gctgttggag cctggagagg gaagtgcatt atgagggctc | 540 |
| tgtcctaagt cagctcccat ccaccaaggg tggtaacgct aagcttttac tctctgctta | 600 |
| aaccatccag caagtcatca agttacaaa agccctgct tagtgcgttc tgggttactt | 660 |
| cattgtgaag atcaggggac tgaagctcag ccagatcaag tgcctcgcct aaggtcatgc | 720 |
| agcttggcca aatccaaacc cttgggtgag tggacagagg agcgtcagct aggagaggtg | 780 |
| ggcgctggtc ttactgggga ggaggggcct gccccctgga ctgctgccct gacctcagcc | 840 |
| ccatcccatt ctgcctagcc ccttgctggg cacttccctc cccagggaca gccacagaaa | 900 |
| aatgatgatc tcggctgggc gtggtggctc acgcctgtaa tcccagcact ttgggaggcc | 960 |
| gaggcaggtg gatcacctta ggtcaggagt tcgagacaaa ccttgccaac atgatgaaac | 1020 |
| cccgtctcta ctaaaaatac aaacattagc tgggcgtggt ggtgtgtgcc tgtagtcccg | 1080 |
| gctacttggg aggctgaggc aggagaatca cttgaacccg gaggcgaagg ttgcagtgag | 1140 |
| ccgagatcaa gccgctgcac tccagctctg ggcaacagag caagactctg cctcgaaaaa | 1200 |
| aataaataaa taagaaagat gatctcaggg tccctacct aggagtcaga tgcacggtgg | 1260 |
| ggccattcct agcgctgcct gccctggaca gcgcctgtct atgcctgtgg cccagcatca | 1320 |
| ttatgaggag tgctccccttg actctggctg tcctgatttg acactagac ttcatggtca | 1380 |
| ccctggccac aggtacccta tcctgcatcc tgagctccgc tcttcctgga gtcatgggct | 1440 |
| ggtctttcct cctggtggcc ttgcgcccca gctccagctt cctgactttt ctcttctgga | 1500 |
| aatgggaatg ccaagtccta tttcatggag ttttgagaat gaaatgactg gtgtacggtg | 1560 |
| caaagtgcct gtgagtgccc aagaaatctc ttttattaac aagacacgaa ttcattccaa | 1620 |
| ttgatttgac gggccactgt tgtcacagca gccgcactgc cccaaaggca gcagtgatgt | 1680 |
| ttgagcgccg actccccgac ggcacttggt cctcacaacc accccatgga gttcatgcta | 1740 |

-continued

```
agatcctcgc atttcatttg tgtggcaggg acttgctgag gtccggggag gggcagagag    1800
gaggggtgcg gccgccccgc gctttgcact ttccgcgtcc tccagcagag gggtcggccg    1860
gcgggctcag cgtcccgcat aatagccgct ttgaagcccg cggagcgggt ggcgggaggg    1920
gaggggagag gcgggagggg aggggagagg cgggagggga ggggcgaggc gggagggagg    1980
gagggagggg ccggcagcgg                                                2000
```

<210> SEQ ID NO 3
<211> LENGTH: 1374
<212> TYPE: DNA
<213> ORGANISM: Artificial Sequence
<220> FEATURE:
<223> OTHER INFORMATION: CRH

<400> SEQUENCE: 3

```
ttgatagtat ttggaggtga aatgaacgag ttttttttta cagactcaat attgaccaat      60
gaaaacatgt aactaatgaa tttagccctg tagtcaagca gtttaagcct ttttcaacat     120
agattaggaa gttagaatgg atgcctctca ttgagtttgc attcagtaga ataagtaaag     180
cttgtttaac tcatgcatct ctcactggcc gcctctctct ttaatttggg aatagaaaag     240
ggagtccaca attaatttta gattgtgaga agagagacaa aaaaaggagc agagagtttc     300
tgagataacc taaaatcttt gccgcacccc ttactaaccc cggtttgtgc cccttcacta     360
tgggagtagc tcttgtcatc atctaaaaaa cttgaactgc attttgagag atttattggc     420
cttgcttctg caggctcata actcctttat gtgcttgctc ttgggaggaa aaagcagata     480
gacgtttaaa agctggatgt tcctgcacac ccctctcctg atgcttcatt cttttccagg     540
cagaaagatg gtgggactct gtctctagca aagggatatt ccagatact gaggtgttgt      600 cagagacacc tggtcaggga ggttaggaga aggggcatcc aggtccaccc cctccaactg     660
gctgctgctt tcctggcagg gctgcactgg gacacctcac ttccttccca cttcccttc      720 ctcctcccat tcgctgtctc tttgcacacc cctaatatgg cctttcatag taagaggtca     780
atatgttttc acacttggga aatctcattc aagaattttt gtcaatggac aagtcataag     840
aagcccttcc attttagggc tcgttgacgt caccaagagg cgataaatat ctgttgatat     900
aattggatgt gagattcagt gttgagatag caaaattctg cccctcgttc cttggcaggg     960
ccctatgatt tatgcaggag cagaggcagc acgcaatcga gctgtcaaga gagcgtcagc    1020
ttattaggca aatgctgcgt ggttttgaa gagggtcgac actataaaat cccactccag     1080
gctctggagt ggagaaactc agagaccaag tccattgaga gactgagggg aaagagagga    1140
gagaaagaaa aagagagtgg gaacagtaaa gagaaaggaa gacaacctcc agagaaagcc    1200
cccggagacg tctctctgca gagaggcggc agcacccggc tcacctgcga agcgcctggg    1260
aaggtaggga gcgcctggac ggaacacgcc accaactttg cgttgcctga gctgccgcga    1320
tgtgcgccgc ggagccggct gcccctgcct gtgtacgtgt gtatgcatgt gtgt          1374
```

<210> SEQ ID NO 4
<211> LENGTH: 1344
<212> TYPE: DNA
<213> ORGANISM: Artificial Sequence
<220> FEATURE:
<223> OTHER INFORMATION: CYP19A1

<400> SEQUENCE: 4

```
ttaataggaa cattgaccaa cttcagtatt cttagaagag catacaggat aagaagaaat      60
taggaaagca tgaaggtcca agtgtttcat aaagtacccc cactgtgggg atatgatgac     120
tgggaggggga tggcagtgat gtaaaaagct ttgtccattt cctcccaact caaacgttct    180
gtgacctact tgaagaactg tcatgtatcc ttatctcttt tcatccaggt atcaggttta    240
gggccaatgg ggaggagcca ctgagaggga gggttgacac tcagcatcat tcagatcttc    300
atttaattca gtaaacactt aactgagcac ttcctgtgcc tggtatgata atgggcattg    360
gagatacgga agtaaaaaag acaggcagat taccctgtga gcagctggaa caccgtggag    420
ccttctgggc ttctctttat cctaacattc attgcagtta ctgttgactg atcatctctc    480
agcaataccc accattaacc atggaataga agcctcctga ggctaggggc catgtcaccc    540
ccaacacata gcacagttcc tgatttggaa ttcactatta cccgttgaat aaatgagtga    600
atgaacgaat gaataaatga aaagctgtat agtgaaggca cttctatgta gaacaatgtg    660
gtgtgtggtg gggggtgtga tcttatgatt acatgtatat agatttttgt ccatggttct    720
tgtccataac tcccatgaca cttgctgagg tcttttgcta taatgtagag gtgctttagg    780
cctcaggaaa cagaatattt ctctggcctt ctttgccctc ctttcatcca cccaaggcgg    840
gactctataa tctgattgtg ggtcataaga ccctcattcc agaggaggtc atgcccata    900
ccctggagga aggaatgctg cacaaagaga ggaagaagaa tctggacaga cagaccttgc    960
tgagattaga tcatacccctt tttgtccaat cacattttgt tcaatcacat gcttcagtca   1020
tggacaacaa atgaaatctc cataaaaggc ccaaaggaca gggttcaggg agtttctgga   1080
gggctgaaca cgtggaggca aacaggaagg tgaagaagaa cttatcctat caggacggaa   1140
ggtcctgtgc tcgggatctt ccagacgtcg cgtatgtatc tcttaatctg actgagccct   1200
caacctgtgg gatcagacac tctttccagg tagatagtgt tggaactgag ttggaggaca   1260
cccagctggt gcccgctgct tggtgtgtgg gggaaaatcc cctacatttg gtcgcagaag   1320
tcttctgtgt tgatgactgt tgtc                                          1344
```

<210> SEQ ID NO 5
<211> LENGTH: 1493
<212> TYPE: DNA
<213> ORGANISM: Artificial Sequence
<220> FEATURE:
<223> OTHER INFORMATION: FBLN1

<400> SEQUENCE: 5

```
tgaacctaac cagcccccga aagcccagca cgctcccact ccaggatcac cactctcctg      60
acctctgaac tgttcttgcc tttttttttt tttttttttt ttttttgagac ggagtctcac    120
tccgccgccc aggctggagt gcagtggtga gatctcggct cactgcaacc tccgtctccc    180
gggttcaggc gattctcctg cctcagcctc ccgagtagct gggactacag gtgtgcacca    240
ccatgcctgg ctaattttat tttattttta tttttagtag agacagggtt tcaccatgtt    300
ggccaggctg gtttcgaact cctgacctca ggcaatccgc ccacttcatc ctcccaaagt    360
gctgggatta caggtgtgag ccaccgccac cggcctgttc ttgcctttta tgtaaatgga    420
atcatgcagc gagtgttcct ttgtggctga ctctattact ctgacttacg tctgtgagat    480
ttacccgtta tgtgagttgc ggatcattca ctcctgttcc gtttgtcgtg ctcctaagcc    540
cgaatactcc acgatattca tctgccttga tgacgctagg cttcccaatt ggaggaatta    600
```

```
tgaatgtgcg gctacatgtc tttctgtctt ttggagcaca tgttgtatgc gtttctgctg      660
agtgtaaggc tgggcggggc gtcggtggct caagggtcc atggtgaact cacaggaaca       720
ccgctttgag ctgcccagtg gcgttcctat gcgtctcatc cagttcctcc gcatcttcac      780
ctgcaccatt ttattcttct tctttggaaa ataaatctac ttgtggttcc aaagcctaac      840
tcatcctcag taacccggt agctatgaat tcctatacaa gaggctcccg caggcccagc       900
gccaaagctg cctcccctgc agcctcgtg acttcccggg tctctccctc cggccctggt       960
gtcccgggtg agcccagcac acgttgggat tttggttgtt tgttggcctg gcccgactgt      1020
ccctgtctct gagggcagag tcgggtccca tcccgggaca cgcctgggt tagccaccga      1080 cctgcagcct cccggccgag ggtgcgggt tggcggtaag gcctgcccca gtgccccca     1140 gcagccgggc ctccgactgc aggcccgggt ccccgctcct ccgcgcggag tcgggcgggg      1200
ataacctttg atcccgagcc ctcccctcga gagggggtgg ggggaggagg ggatcgggtt      1260
tcacggagtg ttggggggata ggactggggg catccggccc gaaggcgccc cctctgtgcc     1320
ccctccgggg aagtctggga tccaggccct cgccccagc cgtgggcgcg cgcccctcgc       1380
agccggggtc cggggaggga gggtccggc aggggcgcc ggggagggag gaccaggaga      1440
cccgcggccc cgcctccgcc gcgccctcct cccgggcggg ataattgaac ggc             1493
```

<210> SEQ ID NO 6
<211> LENGTH: 1326
<212> TYPE: DNA
<213> ORGANISM: Artificial Sequence
<220> FEATURE:
<223> OTHER INFORMATION: GH2

<400> SEQUENCE: 6

```
tgggttagcc tggtcttgca ctcctgacct taagtgatcc acccacctca gcctcccaaa      60
gtgctgggat tataggcatg agccaccgtg cccggcctgg agaaaggact ttaaatgacg      120
caatgtggga agagcaaggt tgtgaagatc tgctgccctg gctgaggtag ctcatgtaat      180
cagtctctct gagcctcagt ctcctgatct gtgaaatggg atgatagtca tagctcctac      240
acaagacaag tggcagttca gacgtgagaa tgcacaggca ggcccttggc aactggataa      300
gctctacaca ggtctggaaa ggaggaggag acaaagagg agggcttcc atggctggat       360 agggcgtctt ttggcgtgat gtgttctgag ttttaaagct ggggaagaga ctcaaatctt      420
caagagctct tccaactttg agattctctg ttggtttcag gactatggga ggaagcgctt      480
gtggtccgtg tctgttcccg ggatttctgt ttcttggttt gtatctctgc tacaggtcca      540
aggagctggg gcaataccct gagtctgggt tattcgtccc cagggacctg ggggagcccc      600 cccccaccc ctcccacacc cacacccacc cccaccccca ccccatccc cacgccccgc        660 cccgccccc gccccaaggc tcaggtaaag gggagagcaa agtgtggagt ttgttccctc       720
tagtggtcag tattagcact gcatccaggc gggcctgtct caggcgagcc caggagtcag     780
caaaagtgga attcagcact gaatcatgcc cagaaccccc gcaatctatt ggctgtgctt      840
tggccccttt tccaacaca cacattctgt ctggtgggtg gagggggaaac atgcggggag      900 gaggaaagga ataggataga gagtgggatg gggtcggtag gggtctcaag gactggctat      960
cctgacatcc ttctccgcgt tcaggttggc caccatggcc tgctgccaga gggcacccac      1020
gtgaccctta aagagaggac aagttgggtg gtatctctgc tgacattctg tgcacaaccc     1080
tcacaacgct ggtgatggtg ggaagggaaa gatgacaagt caggggcat gatcccagca      1140 tgtgtgggag gagcttctaa attatccatt agcacaagcc cgtcagtggc cccaggccta     1200
```

| | |
|---|---|
| aacatgcaga gaaacaggtg aggagaagca gcgagagaga aggggccagg tataaaaagg | 1260 |
| gcccacaaga gaccagctca aggatcccaa ggcccaactc cccgaaccac tcagggtcct | 1320 |
| gtggac | 1326 |

<210> SEQ ID NO 7
<211> LENGTH: 1237
<212> TYPE: DNA
<213> ORGANISM: Artificial Sequence
<220> FEATURE:
<223> OTHER INFORMATION: GULP1

<400> SEQUENCE: 7

| | |
|---|---|
| tctgtccggg ctgaagactg agtaaggtag ggcccctcct tctgcggatg ggtttctctc | 60 |
| tcattccacc ctccacccac ctccggttcc gcgtgcacgc gcgagatagt ccagtgggcc | 120 |
| cacagataac gaccatcaga gattaaagaa ggaaagtcag cgagcttgaa cacaggcgtc | 180 |
| ccgtgtggaa atgtccaagg agaccgccag aagtgcgcaa gccggagtcg gctagagttt | 240 |
| ccttctcacc gagaggggga gcccggcgtt cccggccggg agcgacccgg agtccccagc | 300 |
| cccgcgtccc agctgccgcc agcgccagtt ttggattcgg cggattagga agaggaggga | 360 |
| gggggagag agcgcgaaga gggagggac cgaagctgga gggtcccgag tccagcgccg | 420 |
| tgttggcgta gagaaacttt ccctctcggc ctcggagacg cgccccggc cgtgccggag | 480 |
| tggagatcgc caggctcgga ggaaccggca gctctccacg cccctgcccg aagcctgacc | 540 |
| cgactgcctc tctcagtgag gtacggagat ttatctaggc tcttccctgg ctgcgaaccc | 600 |
| aggctccctc caggtagcgt ggaatcgctt agaagctgat atcccgaggg gcggtggggg | 660 |
| tggacagctc cggccaccag tgcccgggaa ggagggcgcg gggctgcgcg tagccgctgg | 720 |
| ccagcaggtt gtaaaaaatt aggacagcta atgctcagg gagtcgtcca gcactaaagg | 780 |
| aggctaagac ctgttgacgc ctgctatggc agcgcttgag aaatgactgg gggagtccag | 840 |
| cgaggtcggg gacgcagcgg tctccgggct ccagaaacct ccttagcctt ttgtggtaac | 900 |
| tttggtccgg cggcggggg ccggtgagca ggaactggag ggaggcggtg gggaaaccgt | 960 |
| ggatccgtcc ggctgagggt gcgtggatca gactgggctg agcaggcaag tcatcgtcgg | 1020 |
| gtcacagcga ggcgacccag gagcgaactt ccagggcagc ctcccttttg ttggcgctgg | 1080 |
| gagagaatgt gggcatgggg gtggggaggc gcgaagctcc gaggccgggc cgcggatact | 1140 |
| ttaaagctca gagctgggag ggcccaaagg aaggggcggc gtccacatgg ttacccttct | 1200 |
| gctgcgcggg tcaagtagct tcttctggag ggcgcaa | 1237 |

<210> SEQ ID NO 8
<211> LENGTH: 2000
<212> TYPE: DNA
<213> ORGANISM: Artificial Sequence
<220> FEATURE:
<223> OTHER INFORMATION: H19

<400> SEQUENCE: 8

| | |
|---|---|
| gagaaccaag cattaatgcg ctgtggctga tgtgtagtag agcggcattt cccaatggga | 60 |
| gaaccctggg gctgtctagg agcccatgca tggctgggag cctaatccca gggacaccac | 120 |
| cgatgacagc tcccatagca cgtaggacag tggatacttg gaggcaaaga gaaatctctg | 180 |
| ttctgcagtg gtcatgactt ggaccccaaa gaacttgagc ccaaggtcca gagggagacc | 240 |
| ctcccaacag ggcctccagc aggaacaggg atcgtgggag cctgccaagc acagcgcaca | 300 |

-continued

| | |
|---|---|
| ggtatttctg gaggcttccc attcagtctt ggatgccagc ctcaccgagg gcggcccatc | 360 |
| ttgctgacct caccaaggga ggcccgtctc actgccctga tggcgcagaa tcggctgtac | 420 |
| gtgtggaatc agaagtggcc gcgcggcggc agtgcaggct cacacatcac agcccgagca | 480 |
| cgcctggctg gggttcaccc acagaaacgt cccaggtctc ccaggccagg tgccgcattg | 540 |
| gttcccgagg gttgtcagag atagacactc atgcgactaa catcgggcta tgtgtttgat | 600 |
| tcacccagg gtgcattgtt gaaggttggg gagattggag gagatgcttg ggggacaatg | 660 |
| aggtgtccca gttccttgga tgatagggat ctcggcctaa gcgtgagacc cctcctacag | 720 |
| ggtctctggc aggcacagag cctgggggct cttgcatagc acatgtgtat ttctggaggc | 780 |
| ttcccccttcg gtctcaccgc cccgatggtg cagaatcggt tgtagttgtg aatcggaag | 840 |
| tggccgcgcg gcggcagtgc aggctcccac atcacagctc aagcccgccc agctgaggt | 900 |
| tcacccgcgg aaacgtcccg ggtcacgcaa gctaggtgcc gcaaggttca cggggggtagt | 960 |
| gagggataga acactcatgg gagccacatt gggctacgtg tctgattcac cccagggtgc | 1020 |
| actattgagg gttggggaga tgagatactt tggtgacaat gaggtgtccc cattctttgg | 1080 |
| atgatgggga tctcggcctc agcgtgaggc ccctcccaca gggtctctgg caggcacaga | 1140 |
| aactgggggc tcttgcgtag cacatgggta tttgtggacg cttccccttc tgtctcacca | 1200 |
| cccggatggc acagaatcgg ttgtaagtgt ggactcaaaa gtggccgcgc ggcggcagtg | 1260 |
| caggctcaca catcacagcc caagccctcc ctggatgggg ttcgcccgcg gaaacgtcct | 1320 |
| gggtcaccca gccaggtgc cgcagggttc tcggaggtct tctgggaata ggacgctcat | 1380 |
| gggagccaca ccacgtcttc gtatcgggcc atatccacgg ccgcgtggcc ccaggtcaca | 1440 |
| ctctgagggc ttcagtgtca tggcctggga ctcaagtcac gcctaccgc gtgatgagca | 1500 |
| cagcaaattc cgccaaaagc ttatactttc cacatccatc ccagagcaca gatccgacta | 1560 |
| aggacagccc ccaaatcccg agccttttc tgaactgaca attgcctccc cagtgaacac | 1620 |
| tctgagcttg tcaatcttaa gtggccagac attaacattc ccattcagtg caggtttgag | 1680 |
| atgctaattt aggagcttga gatgctaaag agctgggagt gccactgctg ctttattctg | 1740 |
| gggtctagga tccttgtgtt ggctgagata atctgctaat gtgggtgcag cagacatccc | 1800 |
| gcggtttgtg gaatcgataa aggatgggga tcaatggtgt ttgtgcactg tgcggtctgt | 1860 |
| gcccaattgc ctgccttgtg ctgtggaatc tgtacatctg gccaacatgt gcttgtgtga | 1920 |
| gcctgacagt gcatttttcca gagcctcacc tcggctctgc cctggaggct ctgtgctgct | 1980 |
| ggaatcagac tcaaggacct | 2000 |

<210> SEQ ID NO 9
<211> LENGTH: 1316
<212> TYPE: DNA
<213> ORGANISM: Artificial Sequence
<220> FEATURE:
<223> OTHER INFORMATION: HSD3B1

<400> SEQUENCE: 9

| | |
|---|---|
| ctccctgcac aaaacttcat ttcaaaataa tttatatttt aaatatatat ccagaaccac | 60 |
| agagatctta gaagaaaaaa ttagagaaat atagaaataa aatgagaact gtgggaataa | 120 |
| aaatcaggaa gtagttgcct atgaggtaga ttggggggaag gtcagggaat taacagggaa | 180 |
| caggcagaaa acaactttct ggagtgacgg aaatggtcta tatctttttt ggggtgctac | 240 |
| ttacatgggc atatataact gtcaagttcc actgaactga acactgaaga cctgggcatt | 300 |
| ttaatgcatg taaattatat ttcaattttt ttgagtaaag tgtcttggga agcttatggc | 360 |

```
ggtgatattt gggcagttct ggggcatagg cttcagaagc attcacagta tgtccagttc      420
aagaatttgc tgagaatcgt tttgcagcca aaaatatgga taagttcgaa cacctatgat      480
aagagtcatt gggcataca accacaaatc cccactcttg tgatacaggc catatcatta      540
agtggttatc accagatagc tttccttcaa tgatgttgtt catctaggaa cccagggctc      600
tccaggggca aatgaccatt gaggtttcag atatattggg taggaaagaa agtcacctca      660
cataaaacta gtgattgga gctgtcacca ttgcaaattt ctaaattttg taagacagca      720
gcaacatttc aaatgatagt ctgagagagg agataatggg cttacatgga tttccctcca      780
gatggattta ctgaacaagg gcacaattca aattgcactt gcagatttct cctggtctag      840
tttaagttca cagattgtgg atcccagaca gctggtatca actgactagt gtcctgttaa      900
ggctaaaccc aagactcttt gccacactgc agcattagga tgggacttct cttcctgttc      960
ctgggaagaa ttagagatgt aacccaaagg tcactatttt tctgagataa ggatcccata     1020
ggaggagaga gcaatgagta catggccaga gatcaaagtg ataagggttg gccagaagc      1080 cacagtgcat aaagcttcag acttgccaca ggaaatgagg tgagaagtac gtccactctt     1140
ctgtccagct tttaacaatc taactaatgg ttagagattt ttcatttttct ttcagctact     1200 cctgcagtgg tggggacaca gaatgtttgc aaaaaaaatg gggtggagga aaatgaggca     1260
tctgtgtgag tatataacca tttgacatct cttttttagcc ctctccaggg tcaccc        1316

<210> SEQ ID NO 10
<211> LENGTH: 2000
<212> TYPE: DNA
<213> ORGANISM: Artificial Sequence
<220> FEATURE:
<223> OTHER INFORMATION: IGF2

<400> SEQUENCE: 10
gacactcagc agggctggaa ggttggaacc ctcagagtat gaaaattgct tcccataccct      60 tcccccaaat tcggtcatta cacccagagc atgttgaatc cttttctgaa tcataaacga     120
cctgccctct gattgcctga gtttcataaa atggagggat ttccccagtg attccccaaa     180
gctattgaga atgttgtggg tgtgtgagtc acaaagctttt ggggcattaa cgtctatggc     240
tctatatgct gcctggccac gaatcaggtc ccttaagatg tagacagtgc cacccaggtc     300
cctggagcac actgagcagt taccaggagg tgctcaagtg tgacccagga ttctccaggt     360
ccccccaaat cacacagggg ctcccgggtc cctctgggct acaccaagca caaaaggacc     420
ccttgggcag agcctacttt tatttctgtt atgccaggtt ttgctaacgg ccccagttcc     480
caaacattcc gagcactttc tctgcatcac aacatattga ctattaaaca attctctggg     540
tcccaggagc ttcataacaa gaatcttgct tttctaaaat tcaggcattg gtctgaaacc     600
ccaacggcca ggatcacact ggaccctttt cctggtcccc catacttgga tgttctggac     660
gctgccctcc aggccctcta ggaacattca gcattgccct cggatcacag acagcactg      720 atttcttggg ctccaaacaa cccactgagt catctcaaag ttaagcaata tttccttcaa     780
gcacactgca cactccctat cacaaaatct gaaaattcct aagtcctaag acctaggaat     840
tctgaatccc ctttctttaa aatgtacata tggaccccca gtcctccaa ggactctgag      900 caacttccct agatctttag attcaaaaac gattttcctg gagccccaa attgcggtat      960 tgtctcccag ccttccaaag caaattgaga tttttttccc ttcacaaaac aattgaggtt     1020
tttttttttt taatactgat ttatgagtct cctgactttta tggtccctgc cctgggtccc     1080
```

| | |
|---|---|
| cctacattta gaaatgttc catggacccc caaagcacac taaaaaatgt ccctgggtcc | 1140 |
| caagaaatcc caggcatgga aaaacctgcg acctataagt ttcctagcta ctaactaggt | 1200 |
| ttccagaaat ttagatatca aatctccatt gggtaatttc catgtgtccc aaaaacttga | 1260 |
| aatgtgtttc actggggctc ccccaaatgc agacgacatc caggaaaata tatagtcttt | 1320 |
| ttcttattta ccaaaaataa gctaatggaa atcatttaaa aattagcata gaaaaataat | 1380 |
| actgattttt tatttttta ttttttattt tgctttcccc aaatgtactg atcacactcc | 1440 |
| aggctccccc aaaatctaga cagtgctttc ttccatctct gaagggtgtt aaaacctttc | 1500 |
| cctgaagcca cagtaattat gaaggttatt ttttccccgg ctgctgccag cgtccaggcc | 1560 |
| actaacttat attcttaaga tgtgaaaatt aatctcagct tcccctaac acaccaagaa | 1620 |
| tgtgtttgga tccccaaaat gtgttccttg ctttcatctg ccaattttac gtaatatggc | 1680 |
| tctacggcaa aattcccaat ttcatatgga gaattttctt taactacccc tcctcacaaa | 1740 |
| ttggtccccc aagctagctg gcccctattt gagacctctt tctctatgtt cccaattgca | 1800 |
| tggagcaact tctctcatcc cccaaacctg taatctattt ttctggagtc tcgagtttag | 1860 |
| tcattaatca cggttcccac attaacggag tccccggggt cccctcctcc aggacaccca | 1920 |
| ttcgctaagc ccgcaaggca gaaagaactc tgccttgcgt tccccaaaat ttgggcattg | 1980 |
| ttcccggctc gccggccacc | 2000 |

```
<210> SEQ ID NO 11
<211> LENGTH: 1248
<212> TYPE: DNA
<213> ORGANISM: Artificial Sequence
<220> FEATURE:
<223> OTHER INFORMATION: INSL4
```

<400> SEQUENCE: 11

| | |
|---|---|
| ggtgaaacaa cacctctggg gaaactttca tgacaattta acagcagacg taaagcaact | 60 |
| taaaactaaa attttagaat cccttcacat gatagatcta catactcaac aaacagccat | 120 |
| atggaaaggt gtgcaagatc atttctcctg gttataccc cgatcctggg ggtcacactt | 180 |
| tgactggaaa ggaatgttac taattatact catgattgtc ttacgttatt tgctaattct | 240 |
| atgatgcaaa gccggaataa aagcaaaacc taacaaacct gttgctgcac acatctgtac | 300 |
| tcttaagtca acagaacccg atgcaaagaa cagaaagggg ggagatgtga gagttcagtc | 360 |
| aggctggtgg gaaaattttt tcagatagtt ataagaaaaa gacgcaaacc ttttgaaac | 420 |
| gccgaggggg tttgtataag ctccagtaat agatcaggct gaaggcagcc taatccttac | 480 |
| cttgagttaa tagcttaagg cacagataca aatgaatgta gtttatctag tttgtttact | 540 |
| catgtggtcc taagactaat cttttgatcaa ccgcgggtgc ataattgctc tctactcggg | 600 |
| aggttggcaa tgtcaattac cttctagtgg tgtttactca agaccttcgt catttaatct | 660 |
| atgctgaata aatgtgagct ttgctggctg atcggggcca cggctgcaac tctttacagc | 720 |
| accctccttg gtgtctgtag gtggcccgga cccctcagctg gactgacagg caaactatct | 780 |
| gtgtcagtgt atgttattca tccgtcgttg ggtcagggtc tgtgggacag accccgcaa | 840 |
| ttaaaagctt atatgccaaa tgttaactaa gataatttct agccaatgag cttacaggtc | 900 |
| agttctattt ttatttcatc taagcaaagg acattaaaaa ttaccattat tttagtaagc | 960 |
| ataaaaatag tattcagga ggaaagttaa gaaaagaag tagaacaacc aaattcaaaa | 1020 |
| caagcaaagt gcagcagcac attggggagca aagaggata tgagagtgtg gtagggcaa | 1080 |
| gtagggagac taaataagaa ctgagggaga aagttccttg taggtgggtg ggaaagggt | 1140 |

| | |
|---|---:|
| ggaactgaca ccattgacgc aaaagctgag taatagccct aagcaaataa atgcctgatg | 1200 |
| aaggcatgca gaaagcagtc tggagcccag aagggacaca ccagcaca | 1248 |

<210> SEQ ID NO 12
<211> LENGTH: 1373
<212> TYPE: DNA
<213> ORGANISM: Artificial Sequence
<220> FEATURE:
<223> OTHER INFORMATION: LGALS13

<400> SEQUENCE: 12

| | |
|---|---:|
| atgccaatca atgacagatc ggttacagaa aatgtggtac atgtacacaa tgaaatacta | 60 |
| tgcagtccta aaaagaatg atattatgtc ttttgcagga acatggatgg aactggaggc | 120 |
| cattattctt agcaaactaa tgcaggaaca gaaaaccaaa tactgcatgt tctcacttat | 180 |
| cagcgtgaac taaatgagga ggctcatgga catcaagagg aaacaacac acactggggc | 240 |
| ctccttgagg gtggaggatg aaaggtggaa gaggagaaaa aaaataactt ttgagtacta | 300 |
| cacttagtaa ccaggtgaag aaatcatata caccacaaat cccatgacac gactttatct | 360 |
| gcatatgtac cccgaaccta aaataaaatg aagaaaaat caaataaaaa caacaatctc | 420 |
| accttcctcc cagaatctgc aggagaaaca gtgtctctga aactttttatt tacatggaca | 480 |
| ccaagagaaa ggagagggtg tagctagagc ccaggtgtgt gacagtcagg tgagagtggc | 540 |
| ccttacctgg cagagccaag cagcctagtg tggaataggt tcatgcaaga aatttctctg | 600 |
| cttctctcca cagatcctcc tgaggatcaa ggtcagtgct ctcccagaac gttcaaaagc | 660 |
| agagagaatc attaccttct agggctaatg tatttcccca aaatctccaa cttttttctt | 720 |
| ttcagccgtt gtacaaattg gaaaatgta cactttctgg gtatattctg catagatgag | 780 |
| aaaaggcttg agaggcataa aggctgggct ttacaaccac taccgctcac tccatcatct | 840 |
| ttatctatgc atttccctgg taacccaatc cacagcctgg taactccccc actgtcactt | 900 |
| ctgctgcatt acagatacag acctgcaaat agctatggtt gtgactgagt ttcttcctaa | 960 |
| caactaaacc tgtctaaagc tgcaaggaaa tcttgctggg aggagcttgg aatctggaat | 1020 |
| gaagcccgag ggcaaggctg aagtgggtca tttaaatgct gcaactcaga gattcactca | 1080 |
| gaagactgga ctcaattctg aaggtcgcca agaaggagag aacaatgtct tctttacccg | 1140 |
| tgagttgaaa aggcacagcc ttcaaaaatt tcgtgtcaca caaaccaaga agaaatggg | 1200 |
| agattttatg agatgaaaat atgagcattt ttgctgtgaa tgctttactt agagctattg | 1260 |
| aggtgtggaa tagaaaccct gaggctatgg tatctgagat gcttgtgggg attgcgtgt | 1320 |
| ggaccctgga ccagtgtaac cttcggtgag tgtgaggtgg tgtctgatga gca | 1373 |

<210> SEQ ID NO 13
<211> LENGTH: 1267
<212> TYPE: DNA
<213> ORGANISM: Artificial Sequence
<220> FEATURE:
<223> OTHER INFORMATION: MUC15

<400> SEQUENCE: 13

| | |
|---|---:|
| gggccttttgg gcttcagaaa atttaaaact atagaattac cttgttcttt cctcgggcca | 60 |
| attaactggg cagattcttt gcattccatt tgaagcttac tagctcctgc attttagcta | 120 |
| aagtttcgtt tctcgctcag cagttgaaaa cctatctcct tgtgcagcag aaaccaagta | 180 |
| tgaacctcag gcatattgag ctgaacggcc cttggcgcca tccccaaacg ctgatgtgcg | 240 |

| | |
|---|---|
| gaagatccca gtttcactct tctcccttc ataagctctg aaaggaagtg taggaagtat | 300 |
| gccaagttgt tattcaactc tagtatttaa tcaagcatta cctgggcact tctgaaattc | 360 |
| tccagcttct aaagtgagag taaaccagag agaacacagg gtggaaacta cttaatcgag | 420 |
| aaggctccta ggataagtga ggatcacatg gccattctca ggcccagtt cctctccaaa | 480 |
| ctcctgaaag tcagcaagaa accgaatctc agtcatgatg attattttc atgtaacacc | 540 |
| tcacagcgtt ctcagggatc caatatatg ctactaattc actttgtgtt aagtaggagt | 600 |
| ttcttaaaaa aacaatttca gtggacctca gaatagacgc ctcactactg accccactac | 660 |
| atttctcta cttaggcttt aagtacacaa ataggcaat ctactagagt acagaaaaat | 720 |
| tgtttatgat ttcagagaat gtgcggctgg catagagcaa caagtgcagg gcatgacttg | 780 |
| tttggattcc tcacctgcaa ggagcagggg gcccagcaca tgtcagaaat tcctgctata | 840 |
| ccagatgact ttgccaaaat ctttgtcctt ttttcactt agggtgaaaa aaaaaattga | 900 |
| tgacccgtgt tttgctacca ctgacgagag taataccttg tcccaaagct aaaacgatca | 960 |
| acctatgaaa actggagggt tgggcttttg ttgttgttgt taaaggcctg aatgaggtga | 1020 |
| tatcttaatg cttacagctg agaagcaggt cagtcaggtt cctgggcgct ctgttacaca | 1080 |
| agcaagatac agccagcccc acctaatttt gtttccctgg caccctcctg ctcagtgcga | 1140 |
| cattgtcaca cttaacccat ctgttttctc taatgcacga cagattcctt tcagacagga | 1200 |
| caactgtgat atttcagttc ctgattgtaa atacctccta agcctgaagg taagtgtgcg | 1260 |
| ttgggtc | 1267 |

<210> SEQ ID NO 14
<211> LENGTH: 1230
<212> TYPE: DNA
<213> ORGANISM: Artificial Sequence
<220> FEATURE:
<223> OTHER INFORMATION: PAEP

<400> SEQUENCE: 14

| | |
|---|---|
| aaatatcttg ctgagaattt gataggaatt gcattaaatc tctaggttga gttgaggaga | 60 |
| gctaacacct tgctgtgtt gaagcttcca gcccatgaac acattgtgcc tgtcctttac | 120 |
| cttaggtctt tgatttccct tccttgggtt cagagtttaa gtcctgtcca tatttggtga | 180 |
| gattttgcc tacatgctgt gtgtgtgatt acaaatcctg aatttccagt ttcgggttct | 240 |
| gtctactcct tgacactgtg tgggaacacg gtggattttt gtgcgattga ccttgctgac | 300 |
| ctcactcggt tctaggaggg gttttgtaga gttcttgcaa ttttgtacct gggcaatgat | 360 |
| gttatatgcg aatagagaca ggtataccte cccctteca atctgcctgc ctttagttac | 420 |
| catttcttgc ctagctgctc tggccggaat gacctgctct gatggatggg ggagtgggag | 480 |
| tggacacccg tgtcttgcct caggactcaa gtgctctcca gggagtgaga tgcgggctcg | 540 |
| attgtaagtt acaaagtgat gcttccctgt gggaaaaagt acatccaata tagactgtag | 600 |
| gacaaagtct gaaagtccac tgcctcccat ttccacccag tcttgcctgt gagtcagaga | 660 |
| gaaacagtgc taacaggcag tgtgcacctg tccagaggct ggctgtttga gggacacagg | 720 |
| tgtgcacacc tggggatgtc tgagtggaag gtacaggtca ggattatgac cgtgcagtca | 780 |
| gtcacccact ggcatgatgt ctgtggcatc ctggggcagc catgggctc tcaggccctc | 840 |
| tgcctgcccc acaggccata cccctgccct ggacacagct gtcctcagtg ctggcctctg | 900 |
| acccaacatt gtccaggagc cccaacccag aaggtgctcc cgccgctgcc agcctggacc | 960 |
| cgacccaggc ccctcccgcc tgaggccctg ccaagaactg cccagcccgg acacagagga | 1020 |

| | |
|---|---|
| ggttcccgcg tggacgcagg gaagagcctc ccattgcccc agtggaggaa gctgcccagg | 1080 |
| ggccaaggat gagtcacagg ttcgaggaat cacatgcgca ggctgtgggc ggggatcttg | 1140 |
| tctgccctcc tcctacataa ggccccctga gcccacactg cctcagcatc cctctggctc | 1200 |
| cagagctcag agccacccac agccgcagcc | 1230 |

<210> SEQ ID NO 15
<211> LENGTH: 1338
<212> TYPE: DNA
<213> ORGANISM: Artificial Sequence
<220> FEATURE:
<223> OTHER INFORMATION: PKIB

<400> SEQUENCE: 15

| | |
|---|---|
| ttttattagg cgggtgcaga agctactgca gttttttgcca gtactttttt gcaattactt | 60 |
| ttgcactaac ctaatacaaa acaaaatgtg cctacatcac aattcagaaa atcacagct | 120 |
| ttattagcag agtataattt aaggaagtca atcaatcctg aaggcagaaa gacctaagtt | 180 |
| caaaactgat ttggaatctt ctcagctatt tagccttgtt caaagtatct aaccttgctg | 240 |
| aacctcagtt tactatctga aaatagagaa aattattact atattgtgga ggtatgaata | 300 |
| ttgaataatt taaagaactt gattgtacta ccattagcac acactgaata aaatattagt | 360 |
| ctgattatat tttcgtattt ccatatttag gcttttgcct aaaaagggaa tttggaagtg | 420 |
| gtcattggca ggtgtcatag gctttgggtg gcaagtcaga gcatagtatg aatgagcaaa | 480 |
| ttagtaaaga ctagagataa gagaagactt tgagtactaa ttaagagttt caggagacca | 540 |
| gaggagattt taagacttca gtgagaaacc actttctcag gaagcagata aattaattt | 600 |
| atcagcagta tcgtcgtcca tgtaatatgg ctttttaaaaa gcacagtgag accttagtag | 660 |
| taacgacttt attttctta gtgagaacct gaaagtgaaa cttgatatac attattttct | 720 |
| gcttttattg cacaaaaagt tgtttccatt gcatattgct tcctaatctg ttaaaataat | 780 |
| ctgttaacaa actcgaagac ccagattcgg ggcgtagata agcctgtgta ccttcctacc | 840 |
| ttctccaaac agccaacatt agatcaaagg gcaaccttaa tgacacctgg agcacaaacc | 900 |
| ctgctcaggg cgcgtacaac cggagggaca gaaaacacga tgcgacgtcg gaaagcagga | 960 |
| agggaattga aattcccgca gtcacgtcac agaaatctta gcagaacctc atcatcgccc | 1020 |
| aagggaactg ggagtggcgg gcggggagga cgcgggttgt gtgacgatca ccgataatta | 1080 |
| gttggtggtt aacgcacaag taggataaaa gagctcgccc caggctgcca gcagaaaaaa | 1140 |
| gctaccgtgg cacgtgcccc ggggagtgat gcggtggccc ggtttgcacg gagagcggga | 1200 |
| caccgcctgg ggagccgcgc tcgtagcctg ggggcgggac gcggcggccg ctccctccgc | 1260 |
| ccccgagtag ctgccaccgc ctggctgcgc cccagcccag tagctcagac gcggccgcat | 1320 |
| cccggtggac tgtagagg | 1338 |

<210> SEQ ID NO 16
<211> LENGTH: 1249
<212> TYPE: DNA
<213> ORGANISM: Artificial Sequence
<220> FEATURE:
<223> OTHER INFORMATION: PSG1

<400> SEQUENCE: 16

| | |
|---|---|
| cgggatgtgg ccacctaaca ccagctgtcc cttgggaaga cagacctctc ctgtgtgctt | 60 |
| gcgggaagaa ggggaatgtt attgctcttt gatctcagaa cacaactcac ccccacccgc | 120 |

-continued

```
cctctcaggt gagagcaatg tccctccaga caggctctct ggccactgcc tgttcctcct        180
ctacacacag cagcttggcc aggtcaaaac catcaggaca gacccctggg tatgtcagca        240
tatggagggc tgagcccatc atggccacgg agtaagttgg gatgaatctc tccagctctg        300
aacccctgct ctgtcccagg ctcccccctcc cgcatctcaa tgagccatgt cccgcagggt        360
tcctgggtaa ctccccactt cctcctgcac caccacaggg aaggtgtggt gaccacagga        420
cagtcagctg ggcagagaag agaggacatc aaagatggtc aggaagaaca tgagaaacta        480
tgagctccag ctcagccgcc agaccccagg gagccataga ctgacagaga actgtccctt        540
tgactatggg actcacagcc cccactgagc aaccagcaca ggcctctcct cccaagaggc        600
atgagagatt caccctgcac accgccagaa aggacagttt cctctgggac acccaggtcc        660
tgaatgtcca tccttggaag ctgcagccaa gctagacatg attagagaaa ggaagggtcc        720
ctctcaccag gcaacacaca gctcacccac agcacaatgg ggcatcattc tgacagggac        780
ctggtacagc tccagcctcc tgcactgaag gggagagcct gatggggatg aaagaggcca        840
aagggcgtta atttgcaccc cgacccagag ccatggggac accaggaggc tgaggcccag        900
gactgttctt gcccaacctg cagggtatgt gtctgactgt gtgggtctgt gtgtatctct        960
tctgtgtgtg tgtgtgtgtg tgtgtgtgtg tgtgtctgtg tgtctgcaca aagtgtgtct       1020
tgaggtttgg tgaaagaatc actgctgaaa aaggcagagg ccgccacaat tcccagggac       1080
ctgaaacaca gacaaaagga gaaacagaag gagggacaag gaggcaggac ttagagagga       1140
ggggacagag aggtgtcctg ggcctgaccc tgcccatgag cttgagaatt gctcctgccc       1200
tgggaagagg ctcagcacag aaagaggaag gacagcacag ctgacagcc                   1249
```

<210> SEQ ID NO 17
<211> LENGTH: 1635
<212> TYPE: DNA
<213> ORGANISM: Artificial Sequence
<220> FEATURE:
<223> OTHER INFORMATION: PSG3

<400> SEQUENCE: 17

```
cacacggact ctgtcagctc ctccctgacc tggggggccgc caacctaaca ccactccccc         60
tgcagggagc tcctccccac acacctgctc cttccctggg cccagctaaa ggcatctccc        120
agggcagtgc tggtgcacgc gacactacac tgggtgcttt cccctcgtgg cctcccctcca       180 tcctcatcaa ctcgttctgt cactgctccc taaatgcctg cccctgctcc atctgtcctg        240
ttctctgggg catcccaggc caagcctagc actgacacag aacagtggct gcctgagggc        300
ccacagcctc cccgggaatc agccaggcac cctgtgtcct gcctgctccc tgcaccccgg        360
ggggctcaga gcacgtgtga tgctcacaca caggcaccat ccgggatgtg gccacctacc        420
cccagctgtc ccttgggaag acagacctct cctgtgtgct tgctgggaga aggggggatgt       480 tattgctctt tgctcccaga acacaactca ccccacacg cccactcagg tgtgagcaac        540
gtccctccag acaggctctc tggccactac ctgttcctcc tctacacaca gcagcttggc        600
caggtcaaaa acctcaggac agacccctgg gtatgtcggc acatggatgg ctgagcccat        660 catgccaca gagtaagttg ggatgaatct ctccagctct gaaccccctgc tctgtcccag       720 gctccccctc ctgcatctca atgagccatg tccccggggg ttcctgggta actccccact        780
tcctcctgca ccaccacggg aaggtgtggt gaccacagg acaataagct gggcagagaa        840
gagaggacat caaagatggt caggaagaac atgagaaacc atgagctcca gctcagccgc        900
cagaccccag ggagccatag agtgaccgag aactgtccct ttgactatgg gactcacagc        960
```

```
cccccactga gcaaccagca caggcctctc ctcacaagag gcatgagaga ttcatcctgc   1020
acacctccag gaaggacagt ttcctctggg acacccaggt cctgaatgtc catccttgga   1080
agctgcagcc aagctagaca cgattagaaa aggaaggtt ccctctcatc aggcaacaca    1140
cagctcaccc acagcacaat ggggtgtcac tgtgacaggg acctggttca gctccagcct   1200
cctgcactga aggggagagc cagatgggga tgaaagaggc caaagggcat gaatgtgcac   1260
cccgacccag agccatgggg acagcaggag gctgaggccc aggactctgc ttgcccaacc   1320
tgcagggtat gtttctgact gtgtgggtct gtgtgtgtct cttctgtgtg tgtctgtgtg   1380
tgtgtgtgtc tgcacaaagt gtgtgatgag gcttggtgaa agaatcactg ctgaaaaagg   1440
cagaggcctc cacaattccc agggacctga acacagaca aaaggaaaaa caggagggac    1500
aaggaggcag gactgagaga ggaggggaca gagaggtgtc ctgggcctga ccccgcccat   1560
gaacctgaga agtgctcctg ccccgggaag aggctcagcg cagaaggagg aaggacagca   1620
cagctgagag ccatg                                                   1635

<210> SEQ ID NO 18
<211> LENGTH: 1270
<212> TYPE: DNA
<213> ORGANISM: Artificial Sequence
<220> FEATURE:
<223> OTHER INFORMATION: PSG8

<400> SEQUENCE: 18
tgcagggaga agcgggatgt tattgctctt tgctcccaga acacaactca cccccacacg     60
ccccctcagg tgtgagcaag gtccctccag acaggctctc tggccactgc ctgttcctcc    120
tctacacaca gcagcttggc caggtcaaaa ccctcaggac agacccctgg gtatgtcggc    180
acatggaggg ctgagcccat catggccacg gagtaagtca agatgaatct ctccagctct    240 gaaccctgc tctgtcccag gcacaccctc ttgcgtctca acgagccatc tcccttgggg     300
ttcctgggtg actccccact tcctcctgca ccaccacggg gaaggtgtgg tgaccacagg    360
acaatcagct gggcagagaa gagaggacat caaagatggt caggaagaac atgagaaacc    420
ctgagctcca gctcagtggc cagaccccac ggagtcacag agtgaccgag aactgtccct    480
ttgactatgg gactcacagc ccccactgag caaccagcac aggcctctcc tcccaagaga    540
catgagagat tcaccctgca cacctccagg aaggacagtt tcctctggga cacccaggtc    600
ctgagtgtcc atccttggaa gctgcagcca agctagacac gattagagaa aggaagggtc    660
cctctcacca ggcaacacac agctcaccca gcacaatg gggtgtcact gtgacaggga     720
cctggtgcag ctccagcctc ctgcactgaa ggggagagcc agatgggat gaaagaggcc    780 aaagggcatg aatgtgcacc ccgacccaga gccatgggga cagcaggagg ctgaggccca   840
ggactctgct tgcccaacct gcagggtatg tttctgactg tgtaggtctg tgtgtgtcct   900
tctgtgtgtg tgtgtgtgtg tgtgtgtg tgtgtgtgtg tgtgtgtgtc                960
tgcacaaagt gtgtgttgag gtttggtgaa agaatcactg ctgaaaaagg cagaggcctc   1020
cacaattccc agggacctga acacagaca aaaggaaaaa caggagggac aaggaggcag    1080
gactgagaga ggaggggaca gagaggtgtc ctgggcctga ccccgcccat gaacctgaga   1140
ggtgctcctg ccccgggaag aagctcagcg cagaaggagg caggacagca ctgctgagag   1200
ctgtgctcag gaagcttctg gatcctaggc tcatctccac agaggagaac acacagacag   1260
cagagaccat                                                         1270
```

<210> SEQ ID NO 19
<211> LENGTH: 1271
<212> TYPE: DNA
<213> ORGANISM: Artificial Sequence
<220> FEATURE:
<223> OTHER INFORMATION: SPTLC3

<400> SEQUENCE: 19

| | | | | | |
|---|---|---|---|---|---|
| gtgtgtgtgt | ttgattgttt | gtttttgtct | actgccccaa | taaattggtt | tcttttctta | 60 |
| gagtctgatg | ctaaagaagt | ctcgactcag | gaaaaccaca | agggtggact | tgggaagact | 120 |
| caacaggttg | taatgactct | ccagcaaatc | atgtcaccat | gccatttgat | gatggtagga | 180 |
| agaaacaaag | ccttgaagat | tcatgcattg | agagaataag | agttagtgag | taaaccagat | 240 |
| gtgtttcagg | actgggaccc | tgcagtcatc | aaccacctca | cacctgcgtc | agtaacaaac | 300 |
| ccaagctaca | gcatgatttt | tgttctacct | cagcagatat | tttatagatg | gaaaaactga | 360 |
| ggcataaagt | gggtaaatac | ctcccccaag | gtcacgagat | aaagataacg | cagtcatcaa | 420 |
| atattctgtc | tcctcaacat | ctgtcttact | ggaattcttg | atggattggt | accccttat | 480 |
| tatagtactg | attttaacat | aggttggttt | tgaatactgg | gttttaaaa | atcttttcaa | 540 |
| atcatttgta | aattatggaa | atgtatacat | cacatgaaac | ttaccatttt | aatcattttt | 600 |
| aagtgcacag | tttagtttaa | gtacattcac | attgttgtgc | actgatccat | cactatacct | 660 |
| ttttcatctg | ctccagctca | aactctgtac | ccattaaaca | taacttccc | tttgcctcat | 720 |
| ccctccaggc | cctggcaacc | acctctgaat | gctattttat | agcaaaaaga | aatattaact | 780 |
| tttgagcttg | gtttacaacc | aaaaaccaca | attacatgca | ggagagaggg | ggtgggaaaa | 840 |
| agaggttaac | tcagaactca | gttacttaga | agactctgtg | agtgtgctgt | gtgtgtgtgt | 900 |
| ctttaaaaga | ctctccacct | cccagcccgc | ctcctcacac | tttgccactg | ggttgttcag | 960 |
| tccccaggtt | ccctcagtcc | ccagaaggag | ccagcatgga | caatctcctt | tacagtttcg | 1020 |
| gaagcaggtt | tgttgccatg | gagttcacat | tttgacggga | gttgagaagt | ataaaggtaa | 1080 |
| ccatttgttt | tagtttcaac | gatctgacaa | aaagataggc | tgttgctctt | cttctggaaa | 1140 |
| agcctgattg | gtaagattcc | tttaagggct | cagccccaaa | gagctttatc | ccatcccctc | 1200 |
| gcagactgaa | aactaaagcc | tgcagagacc | tctgaaggaa | aacctgtccc | gggctctgtc | 1260 |
| acttcacacc | c | | | | | 1271 |

<210> SEQ ID NO 20
<211> LENGTH: 1679
<212> TYPE: DNA
<213> ORGANISM: Artificial Sequence
<220> FEATURE:
<223> OTHER INFORMATION: TUSC3

<400> SEQUENCE: 20

| | | | | | |
|---|---|---|---|---|---|
| aaggcaggca | acaaaccaca | gtagtattat | cagtacctac | aactttgttt | cctacagaaa | 60 |
| ttattttcat | actcagtaag | ttgttgcaga | tatcttgaac | aattatacgt | atatattcct | 120 |
| taagtattat | atatataata | tttttatatt | ctgtatatat | ttttggagac | agggttttgc | 180 |
| tctgtctccc | aggctggagt | gctgtagcat | gatcggaact | cactgtaacc | tcaaactcct | 240 |
| gggctctagt | gatccttcca | gcctcagtct | tggaatagct | aggactacaa | gtactcccca | 300 |
| ccatacccag | ctgttaattt | tttttttttt | cgtaaagaca | aggtctcact | atcttgccca | 360 |
| ggctgctctc | caactcttgg | acacaagcct | cctgcatagg | tctcccaaag | cattgggttt | 420 |
| acaggtgtga | gccaccgtgc | ctggctaata | ctatgtattt | aatttcatgc | gtttagaaat | 480 |

```
atgtgctatt ttaagaaggc gtctacaggt tttatcacat taccaaaggt gttcatggca    540
caagtgaaga aatctctaga tactagagta ataaaaacca tgatgcatta gaacggatca    600
ggcccatatc aaacgttcaa catacagtct gctgctatgg ttcttttttt ttttttttt    660 ttttttttga gacagagtct cattctgtct cccaggctgg agtgcagtgg agtgatctcg    720
gctcactgca acctctgcct cccgggttta tgccattctc ctgcctcagc ctcccaagta    780
gaggaactgc aaggcgctcc accatgcccg gctactttt gtattttag tagaaatggg    840 gtttccccat gttacggcag gctggtcttg aactcctgac ctcaggtgag ccacctgcct    900
cagcctccca agtgctggga ttacaggca tgagccacca tgtccagtct gctatggttc    960
ttaaaatatt catagaatag aaattgaagt aagtctattc gtttttatat taaaagtagc   1020
tagtacggtg ctctgtactt atgcactcca tggatgctga atgagtcatt gaatgaagtg   1080
gagtctaggt tgtgcctcag gccttccagt ggggctggaa ggaacagttg tgaagttgtg   1140
gggcggcttc tgtgcatcgg gggactctgg agttagatgg tttcccaggg ctctgaagga   1200
gaagagctgt gttcctaata atgatctcaa tgggaataga gattgctggg gaccgcaggg   1260
gccaggttgt cattccccaa agcttcccct tcatcatcca agaaggcatt caggtctttc   1320
tgtgctaggc cccaggtaaa gtgctggact acccagtaat tgggttcagt agcaggatgg   1380
cctcagattg aggtcccagg gccaaaggac cactcctctc ctcagcgctg gtccgggaaa   1440
ggcaagctcc gggcgggagc gcacgccgcg cccccgaagc ctggctccct cgccacgccc   1500
acttcctgcc cccatcccgc gccttttccag gtcttctccc ggtgaaccgg atgctctgtc   1560
agtctcctcc tctgcgtcct cggccgcggc ccgggtccct cgcaaagccg ctgccatccc   1620
ggagggccca gccagcgggc tcccggaggc tggccgggca ggcgtggtgc gcggtagga    1679
```

<210> SEQ ID NO 21
<211> LENGTH: 1326
<212> TYPE: DNA
<213> ORGANISM: Artificial Sequence
<220> FEATURE:
<223> OTHER INFORMATION: HBG1

<400> SEQUENCE: 21

```
gcttagggga taaactaatt tgaagataca gcttgcctcc gataagccag aattccagag     60
cttctggcat tataatctag caaggttaga gatcatggat cactttcaga gaaaacaaa    120 aacaaactaa ccaaaagcaa aacagaacca aaaaccacc ataaatactt cctaccctgt    180
taatggtcca atatgtcaga aacagcactg tgttagaaat aaagctgtct aaagtacact    240
aatattcgag ttataatagt gtgtggacta ttagtcaata aaaacaaccc ttgcctcttt    300
agagttgttt tccatgtaca cgcacatctt atgtcttaga gtaagattcc ctgagaagtg    360
aacctagcat ttatacaaga taattaattc taatccacag tacctgccaa agaacattct    420
accatcatct ttactgagca tagaagagct acgccaaaac cctgggtcat cagccagcac    480
acacacttat ccagtggtaa atacacatca tctggtgtat acatacatac ctgaatatgg    540
aatcaaatat ttttctaaga tgaaacagtc atgatttatt tcaaataggt acggataagt    600
agatattgag gtaagcatta ggtcttatat tatgtaacac taatctatta ctgcgctgaa    660
actgtggctt tatagaaatt gttttcactg cactattgag aaattaagag ataatggcaa    720
aagtcacaaa gagtatattc aaaaagaagt atagcacttt ttccttagaa accactgcta    780
actgaaagag actaagattt gtcccgtcaa aaatcctgga cctatgccta aaacacattt    840
```

```
cacaatccct gaacttttca aaaattggta catgctttag ctttaaacta caggcctcac    900
tggagctaga gacaagaagg taaaaaacgg ctgacaaaag aagtcctggt atcctctatg    960
atgggagaag gaaactagct aaagggaaga ataaattaga gaaaaactgg aatgactgaa   1020
tcggaacaag gcaaaggcta taaaaaaaat tagcagtatc ctcttggggg ccccttcccc   1080
acactatctc aatgcaaata tctgtctgaa acggtccctg gctaaactcc acccatgggt   1140
tggccagcct tgccttgacc aatagccttg acaaggcaaa cttgaccaat agtcttagag   1200
tatccagtga ggccaggggc cggcggctgg ctagggatga agaataaaag gaagcaccct   1260
tcagcagttc cacacactcg cttctggaac gtctgaggtt atcaataagc tcctagtcca   1320
gacgcc                                                              1326

<210> SEQ ID NO 22
<211> LENGTH: 1306
<212> TYPE: DNA
<213> ORGANISM: Artificial Sequence
<220> FEATURE:
<223> OTHER INFORMATION: HBG2

<400> SEQUENCE: 22
aataagccag atttccagag tttctgacgt cataatctac caaggtcatg gatcgagttc     60
agagaaaaaa caaaagcaaa accaaaccta ccaaaaaata aaaatcccaa agaaaaaata    120
aagaaaaaaa cagcatgaat acttcctgcc atgttaagtg gccaatatgt cagaaacagc    180
actgagttac agataaagat gtctaaacta cagtgacatc ccagctgtca cagtgtgtgg    240
actattagtc aataaaacag tccctgcctc ttaagagttg ttttccatgc aaatacatgt    300
cttatgtctt agaataagat tccctaagaa gtgaacctag catttataca agataattaa    360
ttctaatcca tagtatctgg taagagcat tctaccatca tctttaccga gcatagaaga    420
gctacaccaa aaccctgggt catcagccag cacatacact tatccagtga taaatacaca    480
tcatcgggtg cctacataca tacctgaata taaaaaaaat acttttgctg agatgaaaca    540
ggcgtgattt atttcaaata ggtacggata agtagatatt gaagtaagga ttcagtctta    600
tattatatta cataacatta atctattcct gcactgaaac tgttgcttta taggattttt    660
cactacacta atgagaactt aagagataat ggcctaaaac cacagagagt atattcaaag    720
ataagtatag cacttcttat ttggaaacca atgcttacta aatgagacta agacgtgtcc    780
catcaaaaat cctggaccta tgcctaaaac acatttcaca atccctgaac ttttcaaaaa    840
ttggtacatg ctttaacttt aaactacagg cctcactgga gctacagaca agaaggtgaa    900
aaacggctga caaagaagt cctggtatct tctatggtgg gagaagaaaa ctagctaaag    960
ggaagaataa attagagaaa aattggaatg actgaatcgg aacaaggcaa aggctataaa   1020
aaaaattaag cagcagtatc ctcttgggg ccccttcccc acactatctc aatgcaaata   1080
tctgtctgaa acggtccctg gctaaactcc acccatgggt tggccagcct tgccttgacc   1140
aatagccttg acaaggcaaa cttgaccaat agtcttagag tatccagtga ggccaggggc   1200
cggcggctgg ctagggatga agaataaaag gaagcaccct tcagcagttc cacacactcg   1260
cttctggaac gtctgaggtt atcaataagc tcctagtcca gacgcc                  1306

<210> SEQ ID NO 23
<211> LENGTH: 2000
<212> TYPE: DNA
<213> ORGANISM: Artificial Sequence
<220> FEATURE:
<223> OTHER INFORMATION: HBE1
```

<400> SEQUENCE: 23

```
gctgtggaga agctgagaca gtcgtaggag ccttattcat tcaaaccata cgttttcctc    60
tgtgccttt  tcccatatcc tagttccta  gctctcccat ttttgaatac agctgcatta   120
taaaccaaat ttactatgaa gtcctttgct gtggaggcaa tgttgttcca gagtcaacga   180
ggaagactaa tggccaaaac atagtggagg tgctgtgtgt gagtcaacca cttgtaccac   240
tataccactg gggggcccca gtctaagctc tgcttatgcc tatcttgaga tgcaattaca   300
cccaatttcc aatgtgaact cttgcctgag tctcattcat gtgggctatg agaaaaagga   360
tggatatggg agaagaagta gtgataaggg ctgtctctac atggatggaa ggacttggag   420
ggaaactaaa aggtctgaag ttagaagact cacaggtatg aagaacagag gaggaaatgt   480
tgctgcaacc ttttgaaggt cgaggcctgc aactttccca gtgttctttc agcgtttctt   540
cagattttgt gtcctgtagt agctgctacc aggtgctctg gttttccgag ctccctacca   600
ctagcctgac tgaaaagtgg ttatagtttc ttattttat  ctcccctgaa gactatcccc   660
caagcagctt gcacttccag gatttgatgc tgatctctaa gcagatagag atagagcagc   720
aaaggagtca gggtgacttc tcagattcct gaatcttacc gactttatac agtcccttgt   780
agccagatcc agagagttaa ttttttgcaa cttcaagctc aaaactgaag acatactttg   840
tgtatagcat tttgctagct attaggaatt caatatgagc aaaagagttt tactcactgc   900
cctgcctcaa tgaatttatg atcttatagc aagaattgtg caaattgtga ctatataatt   960
cacattatat ataattacaa actatgagaa atggtgtaaa gaaaagatg  aggagctgtg  1020
aaatagcatg aacagggtct tgatctagtc tggggagaaa ggaaaggctt ctgtgagtgt  1080
gtactgcaaa ctagaatcca aaagtggta  agaattaagt aggtaaagct ttcaaggcgg  1140
agggaagagc tttcctgcag aagagctatt atgtacaaag gcactgaggt aggaggtgca  1200
taacacatag aagatgccct tgggatctca gactagatcc ttgtttgcat tcaaggatgc  1260
cttccattaa ccatgtactt ctagggtaaa agtgttgcaa ttcataaatc aagccagtaa  1320
ataatgcttt ccagtccata tgcacacaaa tgtgtcaggt aaacccactg tagagaaacg  1380
cacaaacaca aatacacat  ccacttaaat atgtcttcac atgggtatat tctatgtaca  1440
tatgtacaag catacataca aaacacagtc tgttaaatca gagtttcatc gcaaaatgga  1500
agtgtaaacc taagaaacat tcacagtatt ttcctatcaa ggaagtaaag aggtcttgat  1560
gggggatacc taaaagtggc tgtggtgtgt gtttagatgt cagagactca gtactgggag  1620
agagggaacc tctacttgga gctcaggata ttttgatcag cctgtgtaac ttagagctgc  1680
tagcacacgg tttaaggag  ataaaagcag cctttgggaa acatttatt  ctagcgattt  1740
aggtttcaat gtttaggtgg agcacaaggt tcctgatatg atttggctct gtggccccac  1800
ccaaatctca tcttgtagct cccataattc ccacctgttg tgggagggac ctggtgtgag  1860
atgattgaat catgggggtg ggtctttccc atgctgttct cgtgacagtg aatgggtctc  1920
acgagatctg atggttttaa aaaccggagt tgctctacac aagctctctt tttgcctgct  1980
gccattccag taggatgtga                                              2000
```

<210> SEQ ID NO 24
<211> LENGTH: 3309
<212> TYPE: DNA
<213> ORGANISM: Artificial Sequence
<220> FEATURE:
<223> OTHER INFORMATION: ICP4 upstream flank region

<400> SEQUENCE: 24

```
tctgacctga gattggcggc actgaggtag agatgcccga accccccga gggagcgcgg      60
gacgcgccgg ggagggctgg ggccggggag ggctggggcc ggggagggct ggggccgggg     120
agggctgggg ccggggaggg ctggggccgg ggagggctgg ggccggggag ggctggggct     180
ggggagggct ggggctgggg aggggcggt ggtgtgtagc aggagcggtg tgttgcgccg      240
gggtacgtct ggaggagcgg gaggtgcgcg gtgacgtgtg gatgaggaac aggagttgtt     300
gcgcggtgag ttgtcgctgt gagttgtgtt gttgggcagg tgtggtggat gacgtgacgt     360
gtgacgtgcg gagtgcgccg tgctctgttg gtttcacctg tggcagcccg gccccccgc     420
gggcgcgcgc gcgcgcaaaa aaggcgggcg gcggtccggg cggcgtgcgc gcgcgcggcg     480
ggcgtggggg gcggggccgc gggagcgggg ggaggagcgg ggggaggagc ggggggagga     540
gcggggggag gagcggggg aggagcgggg ggaggagcgg ggggaggagc ggggggagga     600
gcggggggag gagcggggg aggagcgggg ggaggagcgg ggggaggagc ggggggagga     660
gcggggggag gagcggggg aggagcgggg ggaggagcgg ggggaggagc ggggggagga     720
gcggccagac gccgaaaacg ggcccccccc aaaacacacc cccgggggt cgcgcgcggc      780
cctttaaagc ggtggcggcg ggcagcccgg gccccccgcg gccgagacta gcgagttaga     840
caggcaagca ctactcgcct ctgcacgcac atgcttgcct gtcaaactct accaccccgg     900
cacgctctct gtctccatgg cccgccgccg ccgccatcgc ggcccccgcc gccccggcc      960
gcccgggccc acgggcgccg tcccaaccgc acagtcccag gtaacctcca cgcccaactc    1020
ggaacccgcg gtcaggagcg cgcccgcggc cgccccgccg ccgccccccg ccggtgggcc    1080
cccgccttct tgttcgctgc tgctgcgcca gtggctccac gttcccgagt ccgcgtccga    1140
cgacgacgat gacgacgact ggccggacag ccccccgccc gagccggcgc cagaggcccg    1200
gcccaccgcc gccgccccc ggccccggcc cccaccgccc ggcgtgggcc cggggggcgg     1260
ggctgacccc tcccacccccc cctgcgcccc cttccgcctt ccgccgcgcc tcgccctccg    1320
cctgcgcgtc accgcggagc acctggcgcg cctgcgcctg cgacgcgcgg gcggggaggg    1380
ggcgccggag cccccccgcga cccccgcgac ccccgcgacc cccgcgaccc ccgcgacccc    1440
cgcgcgggtg cgcttctcgc cccacgtccg ggtgcgccac ctggtggtct gggcctcggc    1500
cgcccgcctg gcgcgccgcg gctcgtgggc ccgcagcgg gccgaccggg ctcggttccg     1560
gcgccgggtg gcggaggccg aggcggtcat cgggccgtgc ctggggcccg aggcccgtgc    1620
ccgggccctg gcccgcggag ccggcccggc gaactcggtc taacgttaca cccgaggcgg    1680
cctgggtctt ccgcggagct cccgggagct ccgcaccaag ccgctctccg gagagacgat    1740
ggcaggagcc gcgcatatat acgcttggag ccagcccgcc ctcacagggc gggccgcctc    1800
ggggcggga ctggccaatc ggcggccgcc agcgcggcgg ggcccggcca accagcgtcc     1860
gccgagtctt cggggcccgg cccattgggc gggagttacc gcccaatggg ccgggccgcc    1920
cacttcccgg tatggtaatt aaaaacttgc aagaggcctt gttccgcttc ccggtatggt    1980
aattagaaac tcattaatgg gcggccccgg ccgcccttcc cgcttccggc aattcccgcg    2040
gcccttaatg gcaaccccg gtattcccg cctcccgcgc gcgcgtaac cactcccctg       2100
gggttccggg ttatgctaat tgcttttttg gcggaacaca cggcccctcg cgcattggcc    2160
cgcgggtcgc tcaatgaacc cgcattggtc ccctgggtt ccgggtatgg taatgagttt     2220
cttcgggaag gcgggaagcc ccggggcacc gacgcaggcc aagcccctgt tgcgtcggcg    2280
ggaggggcat gctaatgggg ttctttgggg gacaccgggt tgggccccca aatcggggc     2340
```

```
cgggccgtgc atgctaatga tattctttgg gggcgccggg ttggtccccg gggacggggc    2400
cgccccgcgg tgggcctgcc tccctgggga cgcgcggcca ttgggggaat cgtcactgcc    2460 gccccttttgg ggaggggaaa ggcgtggggt ataagttagc cctggcccga cagtctggtc    2520
gcatttgcac ctcggcactc ggagcgagac gcagcagcca ggcagactcg gccgccccc     2580 tctccgcatc accacagaag ccccgcctac gttgcgaccc ccagggaccc tccgtccgcg    2640
accctccagc cgcatacgac ccccatggag ccccgccccg agcgagtac  ccgccggcct    2700 gagggccgcc cccagcgcga ggtgaggggc cgggcgccat gtctgggcg  ccatattggg    2760 gggcgccata ttgggggggcg ccatgttggg ggaccccccga cccttacact ggaaccggcc    2820
gccatgttgg gggacccccca ctcatacacg ggagccgggc gccatgttgg ggcgccatgt    2880 taggggggcgt ggaaccccgt gacactatat atacagggac cggggggcgcc atgttagggg    2940 gtgcggaacc ccctgaccct atatatacag ggaccggggt cgccctgttg ggggtcgcca    3000 tgtgacccccc tgactttata tatacagacc cccaacacat acacatggcc ctttgactc     3060 agacgcaggg cccggggtcg ccgtgggacc ccctgactca tacacagaga cacgccccca    3120
caacaaacac acaaggaccg gggtcgccgt gttgggggcg tggtccccac tgactcatac    3180
gcaggccccc cttactcaca cgcatctagg ggggtgggga ggagccgccc gccatatttg    3240
ggggacgccg tgggacccccc gactccggtg cgtctggagg gcgggagaag agggaagaag    3300
aggggtcgg                                                             3309

<210> SEQ ID NO 25
<211> LENGTH: 1666
<212> TYPE: DNA
<213> ORGANISM: Artificial Sequence
<220> FEATURE:
<223> OTHER INFORMATION: ICP4 downstream flank region

<400> SEQUENCE: 25
cccaggttcc gccggacacc tgcagcaaac ggcaccacgt gcgcggggcc agacgggctc      60
ggcagtatcc catcaggtaa cagtcgcgta tcaggtggcg caggcggttg gcactgccgt     120
gggggtcccg ggcgacccgc aggacccgaa acagctgatt gatacactgg cgcatgtagc     180
ccaggtcggg ggtccatcgt gcgctgctcc gcctctgggc ctggcgcacc gagcgccgta     240
gcattgcatt tgggcttggg gccgacgggg tggggggccg gggctgcgtt tcccgggtag     300
accggacccg ccccatctta ggaaaaataa ccccatcccg ccgatcggga gagctcgtga     360
gccgcaggtt tacccgggcc cgcttgggtc gtgggggaat gtcgtcataa gaccagtcgg     420
acgtgtcgtc gggggtcgtcc gacaccgacg catccgtttc cgtccccgtg gtggattccg     480
ccgacatgtc cagaaaaaac cgcccccccaa gcctccgggg ggccctacgg ccaccgatgc     540 ggggggggcttc atcctggtcc ccagactcgg tcgaatccga tgctgtctcg gattcgacct    600
cagactccaa ggctgtatcg gattctacct cagactccga tgagaggggg cgggaagggc    660
gcttgcgctt gcgcgtgccc aggggcgggg atcggagagc gggacgccgc gcttttacac    720
aaggcgcaaa agcgcctggg gaaatgtcgg ccatccagaa aacgtccggg aggaccacag    780
tggcttcccc ccgcccgacg agcaggaagc ggtccacgac acggtcgccg ccggtcgcct    840
cgacgaggac gttcctcctg cgggaaggca cgaacgcggg tgagccccct cctccgcccc    900
cgcgtccccc ctcctccgcc cccgcgtccc cctcctccg  ccccgcgtc ccccctcctc     960 cgcccccgcg tcccccctcc tccgccccccg cgtcccccccc tcctccgccc acccaaggtg   1020
```

```
cttacccgtg caaaaaaggc ggaccggtgg gtttctgtcg tcggaggccc ccggggtgcg   1080 tccctgtgt ttcgtgggtg gggtgggcgg gtctttcccc ccgcgtccg cgtgtccctt   1140 tccgatgcga tcccgatccc gagccggggc gtcgcgatgc cgacgccgtc cgctccgacg   1200
gccctctgcg actcccgctc ccggtccgcg tgctccgcag ccgctcccgt cgttcgtggc   1260
cggcgccgtc tgcgggcgtc ggtcgcgccg ggcctttatg tgcgccggag agacccgccc   1320
cccgccgccc gggcccgccc ccggggccgg cgcggagtcg ggcacggcgc cagtgctcgc   1380
acttcgccct aataatatat atatattggg acgaagtgcg aacgcttcgc gttctcactt   1440
cttttacccg gcggccccgc cccttgggg cggtcccgcc cgccggccaa tgggggggcg   1500
gcaaggcggg cggcccttgg gccgcccgcc gtcccgttgg tcccggcgtc cggcgggcgg   1560
gaccgggggg cccggggacg gccaacgggc gcgcggggct cgtatctcat taccgccgaa   1620
ccgggaagtc ggggcccggg ccccgccccc tgcccgttcc tcgtta   1666
```

<210> SEQ ID NO 26
<211> LENGTH: 37
<212> TYPE: DNA
<213> ORGANISM: Artificial Sequence
<220> FEATURE:
<223> OTHER INFORMATION: ICP4-1st forward primer 1

<400> SEQUENCE: 26 tttttttgaat tcatggcgtc ggagaacaag cagcgcc                             37

<210> SEQ ID NO 27
<211> LENGTH: 25
<212> TYPE: DNA
<213> ORGANISM: Artificial Sequence
<220> FEATURE:
<223> OTHER INFORMATION: ICP4-1st reverse primer 2

<400> SEQUENCE: 27
tggagccacc ccatggcctc cgcgt                                            25

<210> SEQ ID NO 28
<211> LENGTH: 25
<212> TYPE: DNA
<213> ORGANISM: Artificial Sequence
<220> FEATURE:
<223> OTHER INFORMATION: ICP4-2nd forward primer 3

<400> SEQUENCE: 28
cgacgccgcg cagcagtacg ccctg                                            25

<210> SEQ ID NO 29
<211> LENGTH: 25
<212> TYPE: DNA
<213> ORGANISM: Artificial Sequence
<220> FEATURE:
<223> OTHER INFORMATION: ICP4-2nd reverse primer 4

<400> SEQUENCE: 29 cggcggggc gggcccggcg caccg                                             25

<210> SEQ ID NO 30
<211> LENGTH: 25
<212> TYPE: DNA
<213> ORGANISM: Artificial Sequence
<220> FEATURE:
<223> OTHER INFORMATION: ICP4-3rd forward primer 5

```
<400> SEQUENCE: 30
cctcatgttt gacccgcggg ccctg                                                    25

<210> SEQ ID NO 31
<211> LENGTH: 37
<212> TYPE: DNA
<213> ORGANISM: Artificial Sequence
<220> FEATURE:
<223> OTHER INFORMATION: ICP4-3rd  reverse primer 6

<400> SEQUENCE: 31 tttttttctcg agttacagca ccccgtcccc ctcgaac                                      37

<210> SEQ ID NO 32
<211> LENGTH: 31
<212> TYPE: DNA
<213> ORGANISM: Artificial Sequence
<220> FEATURE:
<223> OTHER INFORMATION: ICP34.5 upstream flank region forward primer

<400> SEQUENCE: 32
aaatcagctg cggtgaaggt cgtcgtcaga g                                             31

<210> SEQ ID NO 33
<211> LENGTH: 31
<212> TYPE: DNA
<213> ORGANISM: Artificial Sequence
<220> FEATURE:
<223> OTHER INFORMATION: ICP34.5 upstream flank region reverse primer

<400> SEQUENCE: 33
aaattctaga gccggcttcc cggtatggta a                                             31

<210> SEQ ID NO 34
<211> LENGTH: 31
<212> TYPE: DNA
<213> ORGANISM: Artificial Sequence
<220> FEATURE:
<223> OTHER INFORMATION: ICP34.5 downstream flank region forward primer

<400> SEQUENCE: 34
aaatgatatc cagcccgggc cgtgttgcgg g                                             31

<210> SEQ ID NO 35
<211> LENGTH: 31
<212> TYPE: DNA
<213> ORGANISM: Artificial Sequence
<220> FEATURE:
<223> OTHER INFORMATION: ICP34.5 downstream flank region reverse primer

<400> SEQUENCE: 35
aaatagatct ctctgacctg agtgcaggtt a                                             31

<210> SEQ ID NO 36
<211> LENGTH: 24
<212> TYPE: DNA
<213> ORGANISM: Artificial Sequence
<220> FEATURE:
<223> OTHER INFORMATION: CSF1PO labeled primer

<400> SEQUENCE: 36
aacctgagtc tgccaaggac tagc                                                     24

<210> SEQ ID NO 37
```

```
<211> LENGTH: 24
<212> TYPE: DNA
<213> ORGANISM: Artificial Sequence
<220> FEATURE:
<223> OTHER INFORMATION: CSF1PO unlabeled primer

<400> SEQUENCE: 37
ttccacacac cactggccat cttc                                           24

<210> SEQ ID NO 38
<211> LENGTH: 20
<212> TYPE: DNA
<213> ORGANISM: Artificial Sequence
<220> FEATURE:
<223> OTHER INFORMATION: D13S317 labeled primer

<400> SEQUENCE: 38
acagaagtct gggatgtgga                                                20

<210> SEQ ID NO 39
<211> LENGTH: 19
<212> TYPE: DNA
<213> ORGANISM: Artificial Sequence
<220> FEATURE:
<223> OTHER INFORMATION: D13S317 unlabeled primer

<400> SEQUENCE: 39
gcccaaaaga cagacagaa                                                 19

<210> SEQ ID NO 40
<211> LENGTH: 20
<212> TYPE: DNA
<213> ORGANISM: Artificial Sequence
<220> FEATURE:
<223> OTHER INFORMATION: D18S51 labeled primer

<400> SEQUENCE: 40
gagccatgtt catgccactg                                                20

<210> SEQ ID NO 41
<211> LENGTH: 20
<212> TYPE: DNA
<213> ORGANISM: Artificial Sequence
<220> FEATURE:
<223> OTHER INFORMATION: D18S51 unlabeled primer

<400> SEQUENCE: 41
caaacccgac taccagcaac                                                20

<210> SEQ ID NO 42
<211> LENGTH: 29
<212> TYPE: DNA
<213> ORGANISM: Artificial Sequence
<220> FEATURE:
<223> OTHER INFORMATION: D16S539 labeled primer

<400> SEQUENCE: 42
gtttgtgtgt gcatctgtaa gcatgtatc                                      29

<210> SEQ ID NO 43
<211> LENGTH: 24
<212> TYPE: DNA
<213> ORGANISM: Artificial Sequence
<220> FEATURE:
<223> OTHER INFORMATION: D16S539 unlabeled primer
```

<400> SEQUENCE: 43
gggggtctaa gagcttgtaa aaag						24

<210> SEQ ID NO 44
<211> LENGTH: 26
<212> TYPE: DNA
<213> ORGANISM: Artificial Sequence
<220> FEATURE:
<223> OTHER INFORMATION: D21S11 labeled primer

<400> SEQUENCE: 44
tgtattagtc aatgttctcc agagac					26

<210> SEQ ID NO 45
<211> LENGTH: 22
<212> TYPE: DNA
<213> ORGANISM: Artificial Sequence
<220> FEATURE:
<223> OTHER INFORMATION: D21S11 unlabeled primer

<400> SEQUENCE: 45
atatgtgagt caattcccca ag						22

<210> SEQ ID NO 46
<211> LENGTH: 26
<212> TYPE: DNA
<213> ORGANISM: Artificial Sequence
<220> FEATURE:
<223> OTHER INFORMATION: D5S818 labeled primer

<400> SEQUENCE: 46
agccacagtt tacaacattt gtatct					26

<210> SEQ ID NO 47
<211> LENGTH: 23
<212> TYPE: DNA
<213> ORGANISM: Artificial Sequence
<220> FEATURE:
<223> OTHER INFORMATION: D5S818 unlabeled primer

<400> SEQUENCE: 47
ggtgattttc ctctttggta tcc						23

<210> SEQ ID NO 48
<211> LENGTH: 21
<212> TYPE: DNA
<213> ORGANISM: Artificial Sequence
<220> FEATURE:
<223> OTHER INFORMATION: D7S820 labeled primer

<400> SEQUENCE: 48
atgttggtca ggctgactat g						21

<210> SEQ ID NO 49
<211> LENGTH: 24
<212> TYPE: DNA
<213> ORGANISM: Artificial Sequence
<220> FEATURE:
<223> OTHER INFORMATION: D7S820 unlabeled primer

<400> SEQUENCE: 49
gattccacat ttatcctcat tgac					24

<210> SEQ ID NO 50

```
<211> LENGTH: 28
<212> TYPE: DNA
<213> ORGANISM: Artificial Sequence
<220> FEATURE:
<223> OTHER INFORMATION: D8S1179 labeled primer

<400> SEQUENCE: 50
accaaattgt gttcatgagt atagtttc                                              28

<210> SEQ ID NO 51
<211> LENGTH: 32
<212> TYPE: DNA
<213> ORGANISM: Artificial Sequence
<220> FEATURE:
<223> OTHER INFORMATION: D8S1179 unlabeled primer

<400> SEQUENCE: 51
attgcaactt atatgtattt ttgtatttca tg                                         32

<210> SEQ ID NO 52
<211> LENGTH: 20
<212> TYPE: DNA
<213> ORGANISM: Artificial Sequence
<220> FEATURE:
<223> OTHER INFORMATION: FGA labeled primer

<400> SEQUENCE: 52
ggctgcaggg cataacatta                                                       20

<210> SEQ ID NO 53
<211> LENGTH: 24
<212> TYPE: DNA
<213> ORGANISM: Artificial Sequence
<220> FEATURE:
<223> OTHER INFORMATION: FGA unlabeled primer

<400> SEQUENCE: 53
attctatgac tttgcgcttc agga                                                  24

<210> SEQ ID NO 54
<211> LENGTH: 18
<212> TYPE: DNA
<213> ORGANISM: Artificial Sequence
<220> FEATURE:
<223> OTHER INFORMATION: TPOX labeled primer

<400> SEQUENCE: 54
cgctcaaacg tgaggttg                                                         18

<210> SEQ ID NO 55
<211> LENGTH: 20
<212> TYPE: DNA
<213> ORGANISM: Artificial Sequence
<220> FEATURE:
<223> OTHER INFORMATION: TPOX unlabeled primer

<400> SEQUENCE: 55
gcacagaaca ggcacttagg                                                       20

<210> SEQ ID NO 56
<211> LENGTH: 21
<212> TYPE: DNA
<213> ORGANISM: Artificial Sequence
<220> FEATURE:
<223> OTHER INFORMATION: TH01 labeled primer
```

```
<400> SEQUENCE: 56
gtgattccca ttggcctgtt c                                              21

<210> SEQ ID NO 57
<211> LENGTH: 22
<212> TYPE: DNA
<213> ORGANISM: Artificial Sequence
<220> FEATURE:
<223> OTHER INFORMATION: THO1 unlabeled primer

<400> SEQUENCE: 57
attcctgtgg gctgaaaagc tc                                             22

<210> SEQ ID NO 58
<211> LENGTH: 24
<212> TYPE: DNA
<213> ORGANISM: Artificial Sequence
<220> FEATURE:
<223> OTHER INFORMATION: Amelogenin labeled primer

<400> SEQUENCE: 58
ccctgggctc tgtaaagaat agtg                                           24

<210> SEQ ID NO 59
<211> LENGTH: 24
<212> TYPE: DNA
<213> ORGANISM: Artificial Sequence
<220> FEATURE:
<223> OTHER INFORMATION: Amelogenin unlabeled primer

<400> SEQUENCE: 59
atcagagctt aaactgggaa ggtg                                           24
```

NON-INVASIVE METHOD AND KIT FOR CAPTURING AND ISOLATING FETAL CELLS FROM MOTHER

CROSS-REFERENCE TO RELATED APPLICATIONS

This application is the U.S. National Stage of International Application No. PCT/CN2017/119951, filed Dec. 29, 2017, which claims the benefit of Chinese Patent Application Number 201611257265.5, filed Dec. 30, 2016. The entire contents of the above-identified priority applications are hereby fully incorporated herein by reference.

TECHNICAL FIELD

The present invention provides a novel prenatal screening and detection method and kit, and, in particular, relates to a non-invasive method and kit capable of realizing capture and isolation of fetal cells in early pregnancy, thereby reducing the risk of giving birth to children with chromosomal diseases or genetic abnormalities.

BACKGROUND

It is rather important to perform prenatal diagnosis in early pregnancy to detect genetic defects such as genetic or chromosomal abnormalities of the fetus. Currently, there are mainly three widely used detection methods for prenatal screening, which are amniocentesis, chorionic villus sampling, and circulating free fetal DNA (cfDNA) testing. However, the current three technologies all have certain limitations. The amniocentesis and the chorionic villus sampling are both invasive procedures that have a certain rate of causing fetal abortion and/or causing fetal damage. In addition, the amniocentesis and the chorionic villus sampling can only be performed for screening and detection at a relatively late time point in pregnancy (8-20 weeks or later).

Prenatal screening of the fetus performed with a maternal blood sample would be a very advantageous option. The extremely limited number of fetal cells existed in the maternal blood has hindered the feasibility of using fetal cells in the maternal circulation for prenatal screening purposes. Fetal cfDNA detection is a recently established diagnostic technique for non-invasive prenatal detection, which utilizes maternal peripheral blood, but this technique cannot reliably detect minor changes in the fetal genome, especially some gene deletions that cause serious diseases or developmental disorders. The fetal cfDNA content in the maternal peripheral blood is extremely low, which also brings certain instability to the results of screening detection.

The existing detection methods for prenatal screening have disadvantages of a late detection window, certain detection risk, low detection rate and poor detection sensitivity. Therefore, there is an urgent need for a method and kit capable of accurately, sensitively, rapidly and specifically capturing and isolating fetal cells from a maternal body fluid in early pregnancy to enable detection of fetal chromosomes and genes for early prenatal screening. In particular, an improved method for isolating fetal cells from a maternal blood sample is needed to facilitate prenatal screening.

SUMMARY OF THE INVENTION

The present invention is based on the specific growth and proliferation of a recombinant herpes simplex virus type I in fetal trophoblast cells or nucleated red blood cells, wherein the recombinant herpes simplex virus type I has the ICP34.5 gene removed, and the ICP4 wild type promoter in the viral genome has been replaced by a promoter of a gene specifically expressed in a fetal trophoblast cell- or nucleated red blood cell, and a fluorescent protein expression cassette is inserted at the position where the gene is removed for the convenient of tracing. Therefore, the present invention is the first to propose the construction of a recombinant herpes simplex virus type I for capturing and isolating fetal cells from maternal body fluid for non-invasive prenatal screening and detection in pregnancy, especially in early pregnancy.

The inventor of the present invention screened out, by analyzing the gene expression profiles of fetal and maternal cells, 20 genes that are specifically expressed in fetal trophoblast cells but not expressed in maternal cells, as well as 3 genes that are specifically expressed in fetal nucleated red blood cells but not expressed in maternal cells. By actively regulating the expression and replication of the recombinant virus with the promoter of the above genes, the recombinant herpes simplex virus type I can specifically replicate and proliferate in fetal trophoblast cells or fetal nucleated red blood cells but does not replicate and proliferate in any of the maternal cells.

In a first aspect, the present invention provides a promoter of a gene specifically expressed in fetal trophoblast cells. Preferably, the promoter is a promoter selected from any one of SEQ ID NO: 1 to SEQ ID NO: 20, or a promoter sequence that is at least 80%, preferably at least 90%, preferably at least 95%, preferably at least 98%, and preferably at least 99% identical to the promoter selected from any one of SEQ ID NO: 1 to SEQ ID NO: 20.

In a second aspect, the present invention provides a promoter of a gene specifically expressed in fetal nucleated red blood cells. Preferably, the promoter is a promoter selected from any one of SEQ ID NO: 21 to SEQ ID NO: 23, or a promoter sequence that is at least 80%, preferably at least 90%, preferably at least 95%, preferably at least 98%, and preferably at least 99% identical to the promoter selected from any one of SEQ ID NO: 21 to SEQ ID NO: 23.

In a third aspect, the present invention provides a recombinant herpes simplex virus type I, which has the pathogenicity-related gene segments removed and replaced the ICP wild type promoter of the viral genome with a promoter of a gene specifically expressed in fetal trophoblast cells or nucleated red blood cells, and which has a marker for tracing the recombinant herpes simplex virus type I inserted. Preferably, the recombinant herpes simplex virus type I has the pathogenicity-related ICP34.5 gene removed.

Preferably, the ICP4 wild type promoter of the viral genome is replaced with a promoter of a gene specifically expressed in fetal trophoblast cells or nucleated red blood cells. Preferably, the promoter of a gene specifically expressed in fetal trophoblast cells is a promoter selected from any one of SEQ ID NO: 1 to SEQ ID NO: 20, or a promoter sequence that is at least 80%, preferably at least 90%, preferably at least 95%, preferably at least 98%, and preferably at least 99% identical to the promoter selected from any one of SEQ ID NO: 1 to SEQ ID NO: 20. Preferably, the promoter of a gene specifically expressed in fetal nucleated red blood cells is a promoter selected from any one of SEQ ID NO: 21 to SEQ ID NO: 23, or a promoter sequence that is at least 80%, preferably at least 90%, preferably at least 95%, preferably at least 98%, and preferably at least 99% identical to the promoter selected from any one of SEQ ID NO: 21 to SEQ ID NO: 23.

Preferably, in the recombinant herpes simplex virus type I, a fluorescent protein expression cassette is inserted at the position where the ICP34.5 gene has been removed. Thus, the virus can specifically express the fluorescent protein during replication and proliferation, which enables an easy and quick distinction between the maternal cells and the fetal cells, and in turns achieves specific capture and/or isolation of the fetal cells. The fluorescent protein expression cassette is selected from the group consisting of a green fluorescent protein expression cassette, a cyan fluorescent protein expression cassette, a red fluorescent protein expression cassette, and a yellow fluorescent protein expression cassette.

In a fourth aspect, the present invention provides a preparation method for preparing a recombinant herpes simplex virus type I of the present invention, the method comprising steps of: (1) replacing a genomic ICP4 wild type promoter of a wild herpes simplex virus type I strain with a promoter of a gene specifically expressed in fetal trophoblast cells or a promoter of a gene specifically expressed in nucleated red blood cells; (2) removing a pathogenic gene from the wild herpes simplex virus type I strain; and (3) inserting a fluorescent protein expression cassette into the genome.

Preferably, the wild-type herpes simplex virus type I strain is a wild-type herpes simplex virus type I strain 17+.

Preferably, the promoter of the gene specifically expressed in fetal trophoblast cells is a promoter selected from any one of SEQ ID NO: 1 to SEQ ID NO: 20, or a promoter sequence that is at least 80%, preferably at least 90%, preferably at least 95%, preferably at least 98%, and preferably at least 99% identical to the promoter selected from any one of SEQ ID NO: 1 to SEQ ID NO: 20.

Preferably, the promoter of the gene specifically expressed in fetal nucleated red blood cells is a promoter selected from any one of SEQ ID NO: 21 to SEQ ID NO: 23, or a promoter sequence that is at least 80%, preferably at least 90%, preferably at least 95%, preferably at least 98%, and preferably at least 99% identical to the promoter selected from any one of SEQ ID NO: 21 to SEQ ID NO: 23.

Preferably, the pathogenic gene, i.e., the ICP34.5 gene, is removed from the wild type herpes simplex virus type I strain.

More specifically, the present invention provides a preparation method for preparing a recombinant herpes simplex virus type I of the present invention, the method comprising steps of:
(1) extracting full-length viral DNA of a wild type herpes simplex virus type I strain;
(2) constructing a plasmid in which a promoter of a gene specifically expressed in fetal trophoblast cells or fetal nucleated red blood cells is linked to an ICP4 gene;
(3) constructing a BHK-ICP4 cell line which stably expresses ICP4;
(4) constructing a plasmid into which a fluorescent protein expression cassette eGFP is inserted and which contains a sequence of the upstream flanking region of the ICP4 gene and a sequence of the downstream flanking region of the ICP4 gene;
(5) constructing a recombinant herpes simplex virus type I with the ICP4 gene removed;
(6) constructing a recombinant herpes simplex virus type I that replaces the ICP4 gene wild type promoter;
(7) extracting full-length viral DNA of the recombinant herpes simplex virus type I obtained in step (6);
(8) constructing a plasmid containing a sequence of the upstream flanking region of ICP34.5 gene and a sequence of the downstream flanking region of ICP34.5 gene; and
(9) constructing a recombinant herpes simplex virus type I with the ICP34.5 gene removed.

More specifically, the present invention provides a preparation method for preparing a recombinant herpes simplex virus type I of the present invention, the method comprising steps of:

(1) extracting full-length viral DNA of a wild type herpes simplex virus type I strain 17+;

(2) constructing a pcDNA3-NHN-Np-ICP4 plasmid:
  (2.1) constructing a pcDNA3-NHN plasmid, and inserting a synthetic nucleotide sequence NheI-HpaI-NheI into the EcoRV site of pcDNA3 to obtain the pcDNA3-NHN plasmid; and
  (2.2) annealing genetically-synthesized single-stranded DNA sequence of a promoter of a gene specifically expressed in fetal trophoblast cells (one of 20 specific genes) or a promoter of a gene specifically expressed in nucleated red blood cells (one of 3 specific genes) to form double-stranded DNA, and inserting the double-stranded DNA into NruI/HindIII site of the pcDNA3-NHN obtained in (2.1) to form a series of plasmids, which are collectively referred to as pcDNA3-NHN-Np;
  (2.3) amplifying ICP4 gene by a three-stage PCR by taking the full-length viral DNA obtained in step A as a template and using primers shown in Table 1 below:

TABLE 1

```
ICP4-1st  Forward Primer 1 tttttttgaattc147105atggcgtcggagaacaagcagcgcc147129
          Reverse Primer 2 148279tggagccaccccatggcctccgcgt148255

ICP4-2nd  Forward Primer 3 148205cgacgccgcgcagcagtacgccctg148229
          Reverse Primer 4 149739cggcggggcgggcccggcgcaccg149715

TCP4-3rd  Forward Primer 5 149675cctcatgtttgacccgcgggccctg149699
          Reverse Primer 6 tttttctcgag151001ttacagcacccgtcccctcgaac150977
```

(2.4) treating the ICP4-1st sequence obtained in step (2.3) with EcoRI/BsrGI, the ICP4-2nd sequence obtained therein with BsrGI/PvuI, and the ICP4-3rd sequence obtained therein with PvuI/XhoI; and (2.5) inserting the gene sequences obtained in step (2.4) into the EcoRI/XhoI site of the pcDNA3-NHN-Np plasmid obtained in step (2.2), to obtain pcDNA3-NHN-Np-ICP4 plasmid in which the promoter of the gene specifically expressed in fetal trophoblast cells (20 specific genes) or the promoter of the gene specifically expressed in nucleated red blood cells (3 specific genes) is linked to the ICP4 gene;

(3) constructing a BHK-ICP4 cell line stably expressing ICP4:
  (3.1) constructing a pcDNA3-CMV-ICP4 plasmid, treating the pcDNA3-NHN-Np-ICP4 plasmid obtained in (2.5) with EcoRI/XhoI to obtain an ICP4 gene expression cassette, and inserting the ICP4 gene expression cassette into the EcoRI/XhoI site of a pcDNA3 plasmid to obtain the pcDNA3-CMV-ICP4 plasmid; and
  (3.2) transfecting BHK cells with the pcDNA3-CMV-ICP4 plasmid obtained in (3.1) to obtain, by screening, a stable cell line BHK-ICP4;
(4) inserting a fluorescent protein expression cassette eGFP into the EcoRV site of a pICP4del plasmid containing an upstream flanking region sequence and a downstream flanking region sequence of the ICP4 gene to obtain a pICP4delGFP plasmid;
(5) constructing a recombinant herpes simplex virus type I, oHSV1-d4GFP, with the ICP4 gene removed:
  (5.1) co-transfecting the full-length viral DNA of the wild type herpes simplex virus type I strain 17+ obtained in step (1) and the pICP4delGFP plasmid obtained in step (4) into the BHK-ICP4 cells obtained in (3.2), wherein homologous recombination occurs between the ICP4 gene on the full-length viral DNA and the fluorescent protein expression cassette on the pICP4delGFP plasmid, resulting in fluorescent plaques of the recombinant virus; and
  (5.2) the fluorescent plaque is selected and purified to obtain the recombinant herpes simplex virus type I, oHSV1-d4GFP;
(6) constructing a recombinant herpes simplex virus type I 17+NpICP4 with the wild-type promoter of ICP4 gene replaced:
  (6.1) treating the pcDNA3-NHN-Np-ICP4 plasmid obtained in (2.5) with PmeI/HpaI to obtain an Np-ICP4 gene expression cassette, and inserting the Np-ICP4 gene expression cassette into the SalI/BE site of the pICP4del plasmid to obtain a pICP4del-Np-ICP4 plasmid;
  (6.2) co-transfecting the viral DNA of the recombinant herpes simplex virus type I oHSV1-d4GFP obtained in step (5.2) and the pICP4del-Np-ICP4 plasmid obtained in step (6.1) into the BHK-ICP4 cells, wherein homologous recombination occurs between the oHSV1-d4GFP fluorescent protein expression cassette and the ICP4 gene expression cassette linked to the promoter of the gene specifically expressed in fetal trophoblast cells (20 specific genes) or the promoter of the gene specifically expressed in nucleated red blood cells (3 specific genes) on the pcDNA3-NHN-Np-ICP4 plasmid, resulting in non-fluorescent plaques of the recombinant virus; and
  (6.3) the non-fluorescent plaque is selected and purified to obtain the recombinant herpes simplex virus type I 17+NpICP4;
(7) extracting full-length viral DNA of the recombinant herpes simplex virus type I 17+NpICP4 obtained in step (6.3);
(8) constructing a plasmid pH2dI34.5 containing an upstream flanking region sequence and a downstream flanking region sequence of ICP34.5 gene:
  (8.1) PCR-amplifying the upstream flanking region sequence and the downstream flanking region sequence of the ICP34.5 gene by using the full-length viral DNA obtained in step (1) as template and using primers shown in Table 2 below:

TABLE 2

| Amplification of the upstream flanking region sequence of the ICP34.5 gene | Forward Primer | AAATCAGCTG$^{124356}$CGGTGAAGGTCGTCGTCAGAG$^{124376}$ |
| | Reverse Primer | AAATTCTAGA$^{125661}$GCCGGCTTCCCGGTATGGTAA$^{125641}$ |
| Amplification of the downstream flanking region sequence of the ICP34.5 gene | Forward Primer | AAATGATATC$^{126943}$CAGCCCGGGCCGTGTTGCGGG$^{126963}$ |
| | Reverse Primer | AAATAGATCT$^{127640}$CTCTGACCTGAGTGCAGGTTA$^{127620}$ |

(8.2) inserting the PCR product of the upstream flanking region sequence obtained by the amplification in step (8.1) into the PvuII/XbaI site of pSP72 plasmid to obtain a pSP72H2d34.5US plasmid;
  (8.3) inserting the PCR product of the downstream flanking region sequence obtained by amplification in step (8.1) into the EcoRV/BglII site of the pSP72H2d34.5US plasmid obtained in step (8.2) to obtain a pH2d34.5 plasmid containing the upstream flanking region sequence and the downstream flanking region sequence of the ICP34.5 gene; and
  (8.4) inserting the fluorescent protein expression cassette into the EcoRV site of the pH2d34.5 plasmid obtained in step (8.3) to obtain a pH2d34.5GFP plasmid;
(9) constructing a recombinant herpes simplex virus type I 17+NpICP4d34.5GFP, with the ICP34.5 gene removed:
  (9.1) co-transfecting the full-length viral DNA of the recombinant herpes simplex virus type I 17+NpICP4 obtained in step (7) and the pH2d34.5GFP plasmid obtained in step (8.4) into the BHK-ICP4 cells, wherein homologous recombination occurs between the ICP34.5 gene on the full-length viral DNA and the fluorescent protein expression cassette on the pH2d34.5 fluorescent protein plasmid, resulting in fluorescent plaques of the recombinant virus; and
  (9.2) the fluorescent plaque is selected and purified to obtain a series of recombinant herpes simplex virus type I 17+NpICP4d34.5GFP.

In a fifth aspect, the present invention provides a recombinant herpes simplex virus type I prepared by the preparation method in the fourth aspect.

In a sixth aspect, the present invention provides a diagnostic kit for prenatal screening during pregnancy, preferably early pregnancy, wherein the kit comprises the recombinant herpes simplex virus type I of the present invention. Preferably, the kit of the present invention comprises the recombinant herpes simplex virus type I in the above third aspect. Preferably, the kit of the present invention comprises the recombinant herpes simplex virus type I prepared by the preparation method in the fourth aspect.

In addition to the recombinant herpes simplex virus type I of the present invention which satisfies a certain titer, the kit of the present invention may further comprise a red blood cell lysing solution and a phosphate buffer, or Ficoll-Urografin and a phosphate buffer. Preferably, the virus titer is $1\times10^7$ cfu. Preferably, the red blood cell lysing solution has a pH of 7 and is consisted of 0.15M ammonium chloride, 10 nM potassium bicarbonate and 1n Methylenediaminetetraacetic acid, and the phosphate buffer has a pH of 7.3. Preferably, the Ficoll-Urografin has a specific density of $1.077\pm0.001$ kg/m$^3$, and the phosphate buffer has a pH of 7.3. Preferably, the kit of the present invention may also be composed of the recombinant herpes simplex virus type I of the present invention which satisfies a certain titer alone.

In a seventh aspect, the present invention provides a method for isolating fetal cells from a maternal blood sample in pregnancy, preferably in early pregnancy, the method comprising steps of: (1) collecting peripheral blood of a pregnant woman of a certain gestational age, and adding a red blood cell lysing solution; (2) after the red blood cells are lysed, centrifuged and washed with a phosphate buffer (PBS), re-suspending the cells in RPMI-1640; (3) mixing the cells obtained in step (2) with a recombinant herpes simplex virus type I suspension ($10^6$ Pfu/ml) of the present invention, and adding the resulting mixture to wells of a multi-well culture plate; (4) incubating the multi-well culture plate in an incubator containing 5% $CO_2$ at 37° C.; (5) after 24 hours, collecting the cells, which are washed and re-suspended in PBS, and adding a fluorescently labeled anti-CD45 antibody (a fluorescently labeled antibody against the leukocyte surface marker CD45) thereto, followed by incubation at room temperature for 30 minutes in the dark; and (6) gently washing the cells with PBS, and after re-suspending, sorting CD45−/GFP+ cells by flow cytometry to obtain fetal cells.

More specifically, the present invention provides a method for isolating fetal cells from a maternal blood sample in pregnancy, preferably in early pregnancy, the method comprising steps of:
 (1) taking 5 ml of peripheral blood from a pregnant woman in 8 weeks of pregnancy with an EDTA anticoagulation tube, and adding 45 ml of a red blood cell lysing solution, followed by incubation at room temperature for 10 minutes;
 (2) after the red blood cells are lysed, performing centrifugation (800 g, 10 minutes);
 (3) removing the supernatant, and re-suspending cell pellet in 10 ml of phosphate buffer (PBS) with a pH value of 7.3, followed by centrifugation (800 g, 10 minutes);
 (4) removing the supernatant, and re-suspending cell pellet in 2 ml RPMI-1640;
 (5) mixing 2 ml of the cells obtained in step (4) with 0.1 ml of a recombinant herpes simplex virus type I suspension ($10^6$ Pfu/ml) of the present invention, and adding the resulting mixture to wells of a six-well culture plate;
 (6) incubating the culture plate in an incubator containing 5% $CO_2$ at 37° C.;
 (7) after 24 hours, collecting the cells, and pipetting the cells into a centrifuge tube, followed by centrifugation (500 g, 5 minutes);
 (8) discarding the supernatant, and adding 3 ml of PBS in each centrifuge tube for gently washing the cells, followed by centrifugation (500 g, 5 minutes);
 (9) removing the supernatant, re-suspending cell pellet in 0.4 ml of PBS, adding 100 μl of a fluorescently labeled anti-CD45 antibody (a fluorescently labeled antibody against the leukocyte surface marker CD45), followed by incubation at room temperature for 30 minutes in the dark;
 (10) after 30 minutes, gently washing each centrifuge tube with 4 ml of PBS, followed by centrifugation (500 g, 5 minutes); and
 (11) after the centrifugation is completed, discarding the supernatant, adding PBS for re-suspending, and sorting CD45−/GFP+ cells by flow cytometry.

Preferably, the above method can be carried out using the kit of the present invention to isolate fetal cells from a maternal blood sample in pregnancy, preferably in early pregnancy.

In an eighth aspect, the present invention provides use of the recombinant herpes simplex virus type I in the above third aspect or the recombinant herpes simplex virus type I prepared by the preparation method in the fourth aspect in isolating fetal cells from a maternal blood sample in pregnancy, preferably in early pregnancy.

In a ninth aspect, the present invention provides use of the recombinant herpes simplex virus type I in the above third aspect or the recombinant herpes simplex virus type I prepared by the preparation method in the fourth aspect in prenatal screening.

In a tenth aspect, the present invention provides use of the kit in the sixth aspect in isolating fetal cells from a maternal blood sample in pregnancy, preferably in early pregnancy.

In an eleventh aspect, the present invention provides use of the kit in the sixth aspect in prenatal screening.

In summary, the recombinant herpes simplex virus type I of the present invention can specifically capture an extremely small amount of active trophoblast cells or nucleated red blood cells from any sample to be tested containing active trophoblast cells or nucleated red blood cells, such as maternal peripheral blood and cervical Pap smear, and has characteristics of simple operation, rapidity, good reproducibility, high capture sensitivity and specificity.

The present invention provides a recombinant herpes simplex virus type I and a kit for accurate, sensitive, specific and safe capture and isolation of fetal cells, as well as preparation methods and uses thereof. Since the trophoblast cells develop to form placenta and the nucleated red blood cells are cells of the fetal circulatory system, they carry the same genome as the developing embryo and fetus. Thus, capturing and isolating the trophoblast cells or the nucleated red blood cells, and extracting DNA from the cells, can provide the same or more comprehensive information as compared to other prenatal testing methods, with an earlier detection time and a less invasiveness.

The specific capture of trophoblast cells or nucleated red blood cells is the merit of the present invention. By analyzing the gene expression profiles of fetal and maternal cells, 20 genes, which are specifically expressed in fetal trophoblast cells but not expressed in the maternal cells, and 3 genes, which are specifically expressed in fetal nucleated red blood cells but not expressed in the maternal cells, were screened out. The recombinant herpes simplex virus type I can specifically replicate and proliferate in fetal trophoblast cells or fetal nucleated red blood cells, but does not replicate or proliferate in any of the maternal cells, which has been achieved by actively regulating the expression and replication of the virus with the promoter of the above genes. The virus can specifically express a fluorescent protein during replication and proliferation, so that the maternal and fetal cells can be easily and quickly distinguished, thereby achieving the specific capture and isolation of the fetal cells.

The present invention overcomes the shortcomings of the existing prenatal screening detection means, i.e., a late detection window, certain detection risk, low detection rate and poor detection sensitivity, and provides a series of recombinant herpes simplex virus type I strains, which can be used to rapidly, accurately, sensitively and specifically capture and isolate rare fetal cells for early prenatal screening.

DETAILED DESCRIPTION OF THE EMBODIMENTS

Figure 1:
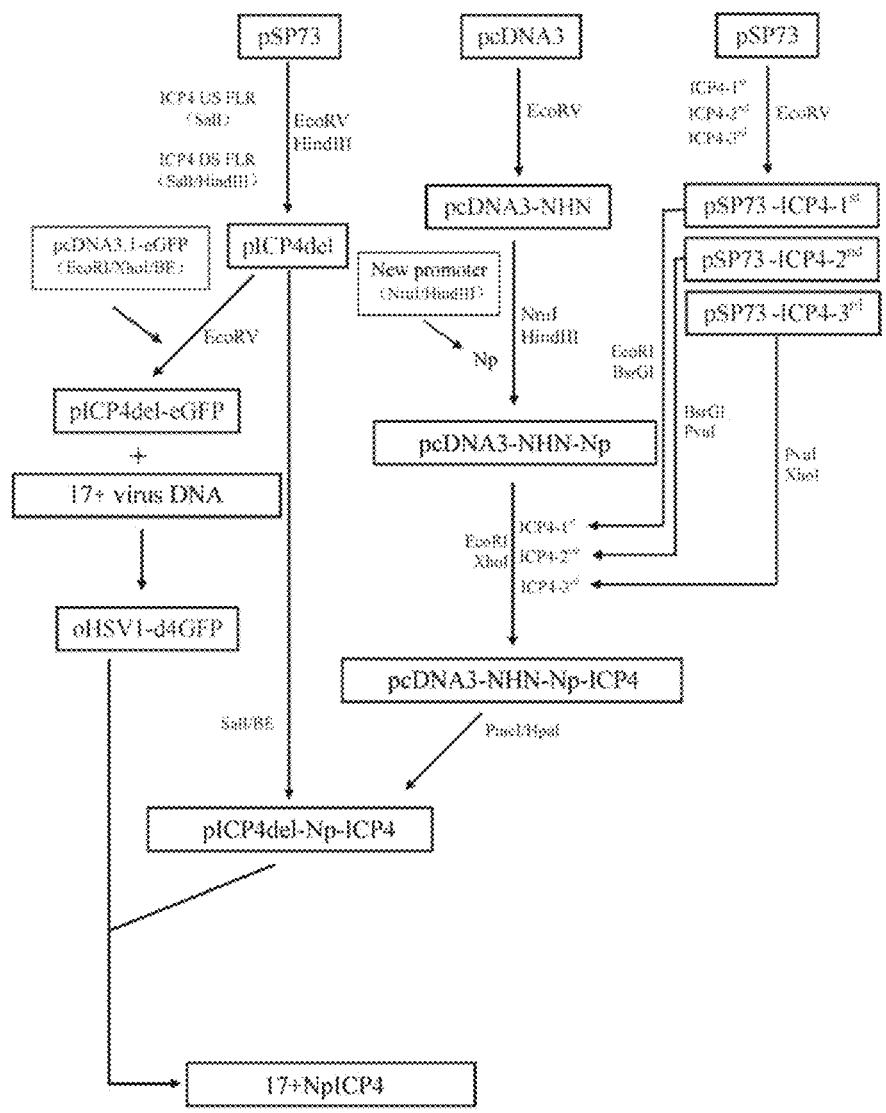
FIG. 1 shows the construction of a pICP4delGFP plasmid; the construction of a recombinant herpes simplex virus type I with ICP4 gene removed (oHSV1-d4GFP); the construction of a pcDNA3-NHN-Np-ICP4 plasmid; and the construction of a recombinant herpes simplex virus type I 17+NpICP4 that replaces the ICP4 gene wild type promoter.
Figure 2:
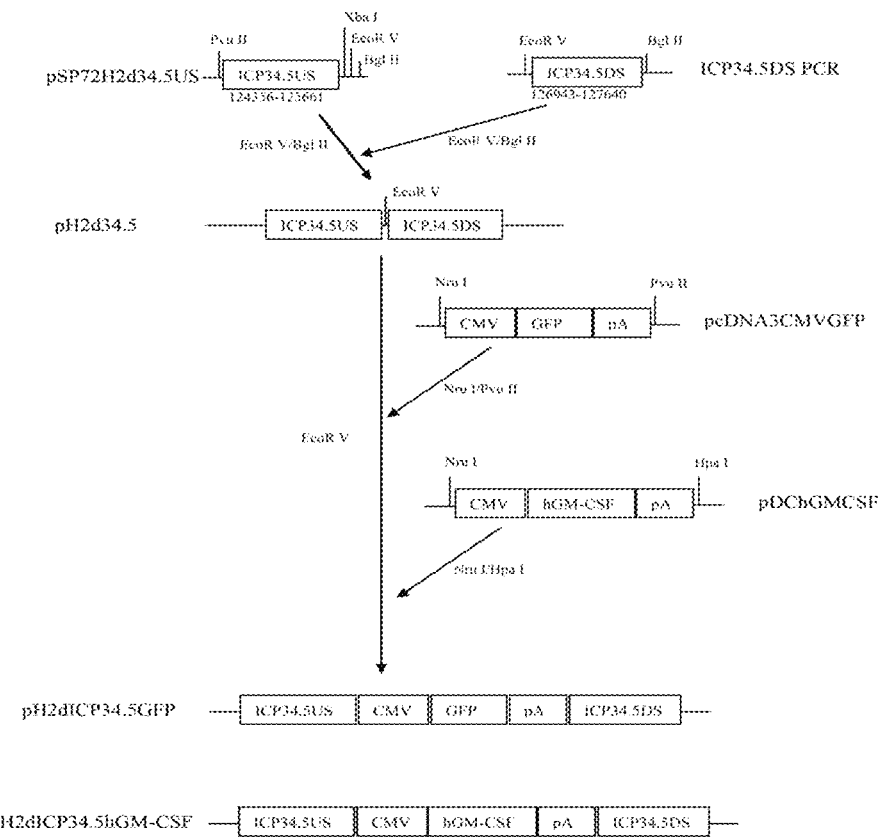
FIG. 2 illustrates the preparation of a pH2d34.5GFP plasmid.

After the embryo develops into morula, the morula is further developed, cells begin to differentiate, and the smaller cells that accumulate at one end of the embryo are trophoblast cells, which will develop into fetal membrane and placenta at a later stage. Therefore, in general, taking a small amount of trophoblast cells during genetic diagnosis of a fetus does not affect the development of the fetus, but belongs to an invasive screening method. Fetal nucleated red blood cells are stably present in the peripheral blood of pregnant women and are cells of the fetal circulatory system, fetal erythroid cells develop earlier than leukocytic cells in early pregnancy, and the fetal nucleated red blood cells entering the maternal peripheral blood are more than other types of fetal cells in early pregnancy. The fetal trophoblast cells and fetal nucleated red blood cells have the same genome as the developing embryo and fetus; capturing and isolating the fetal trophoblast cells or fetal nucleated red blood cells and extracting chromosomes and DNA from these cells can be adopted for the screening of fetal hereditary diseases. In addition, the detection time can be earlier and the detection can be less invasive.

The herpes simplex virus type I (HSV-I) is a double-stranded DNA virus, with a host profile including a large number of mammals and birds, which does not integrate into the host genomic chromosomes after entering the host cells, is easy to manipulate and has a great capacity to package exogenous genes, and into which an exogenous gene up to 50 kb long can be inserted. The ICP34.5 gene of the herpes simplex virus type I is a pathogenic gene, and the product thereof renders the endogenous antiviral interferon system of the host ineffective and thus exerts a pathogenic effect.

Various fluorescent protein expression cassettes available in the art can be inserted into the recombinant herpes simplex virus type I of the present invention. The fluorescent protein expression cassette is preferably selected from the group consisting of a green fluorescent protein expression cassette, a cyan fluorescent protein expression cassette, a red fluorescent protein expression cassette, and a yellow fluorescent protein expression cassette. The green fluorescent protein expression cassette is most preferred. The color of the fluorescent protein (green, cyan, red, yellow, etc.) is determined by which known wavelength range of the visible spectrum the fluorescent emission light thereof falls into. The cyan (blue) fluorescent protein is formed by mutating the tyrosine residue at position 66 of the green fluorescent protein to histidine. This transition causes the blue emission light to have a maximum wavelength of 450 nm, and after mutation to tryptophan, the peak of the fluorescence can be 480 nm. The red fluorescent protein can be derived from corals, jellyfish and anemones (e.g., Discosomastriata). The peak of the fluorescence emission spectrum of the red fluorescent protein DsRed from Discosomastriata is 583 nm and the main peak of the excitation spectrum is 558 nm, and other minor peaks are around 500 nm. The yellow fluorescent protein can obtain a dipole moment of the stable chromophore in an excited state by mutating threonine at position 203 of the green fluorescent protein to tryptophan, thereby increasing the wavelengths of both the excitation light and the emitted light by 20 nm. The enhanced yellow fluorescent protein (EYFP) is one of the most widely used and brightest fluorescent proteins available. The fluorescence emitted by the fluorescent protein can be quantitatively or qualitatively detected by conventional detection means and instruments such as a fluorescence microscopy or a flow cytometry.

The recombinant herpes simplex virus type I obtained by the present invention can be preserved by a conventional method. For example, for short-term preservation, the virus can be directly stored or suspended in 50% glycerin saline and placed in a refrigerator at −30° C. For long-term preservation, the following can be adopted:

(1) A low temperature flash freezing method, in which the virus suspension is added with inactivated animal serum or other protein protectants, preferably with additional dimethyl sulfoxide (e.g., 5% to 10%), followed by flash freezing and preservation at −70° C. or −196° C. A tissue material containing the virus may be directly cryopreserved, and may also be first immersed in 50% glycerol buffered saline and then cryopreserved (at −70° C. or −196° C.).

(2) A freeze-drying method, in which the frozen virus suspension is dehydrated under vacuum. Usually, a low-temperature dehydration method is used, and excess water vapor, which has not been condensed in the condenser, is removed by a desiccant or condensation method. Common desiccants include phosphorus pentoxide, calcium sulfate, calcium chloride and silica gel. When the virus is freeze-dried, a defatted milk, an inactivated normal animal serum, a saturated sucrose solution or the like is generally used as a protective agent. During vacuum drying, the virus suspension is mixed with 5-10 times the amount of the protective agent, the resulting mixture is dispensed in ampoules, with a content of 0.2-0.5 ml for each, and the ampoules are immediately frozen in pre-cooled −30° C. to −40° C. alcohol for 1-2 hours, then quickly placed in a dryer with desiccants and immediately evacuated and dried. After sufficient drying, the dryer is opened to take out the ampoules of dried strain, which are evacuated to make them vacuum and sealed on the flame. Such freeze-dried strains can generally be preserved in a 4° C. refrigerator for several years to more than a decade. Thus, the dry powder of the recombinant type II herpes simplex virus of the present invention can be obtained.

EXAMPLES

Figure 3:
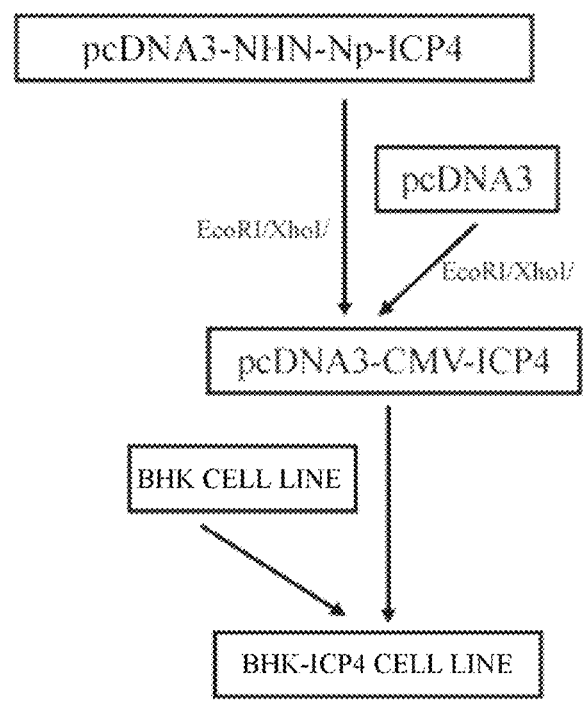
FIG. 3 illustrates the preparation process of a stable cell line BHK-ICP4.
Figure 4:
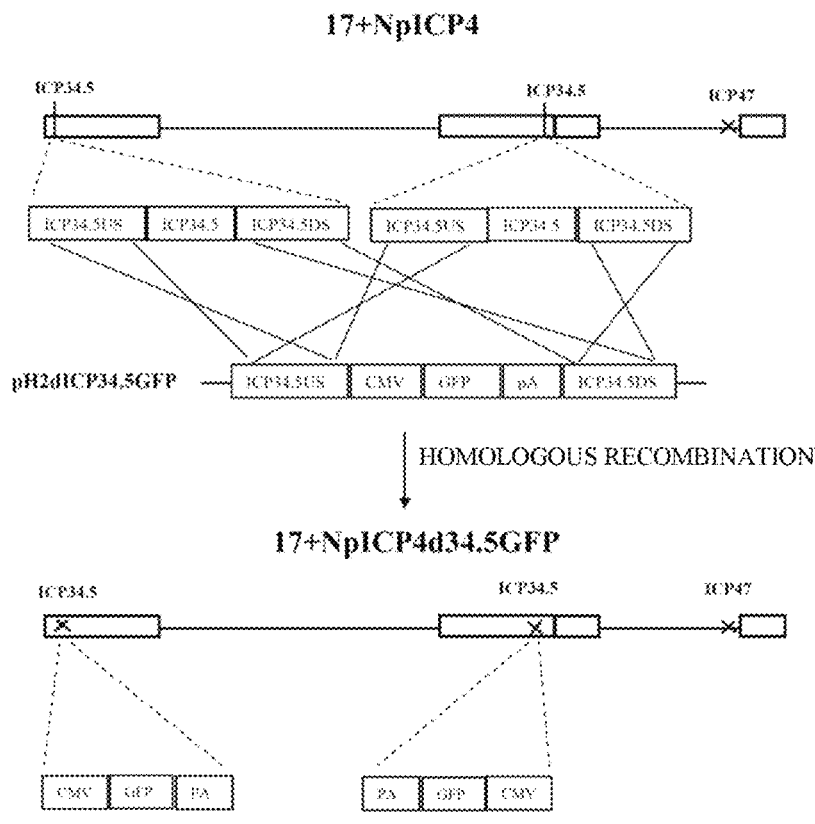
FIG. 4 shows the construction of a recombinant herpes simplex virus type I 17+NpICP4d34.5GFP, with ICP34.5 gene removed.
Figure 5:
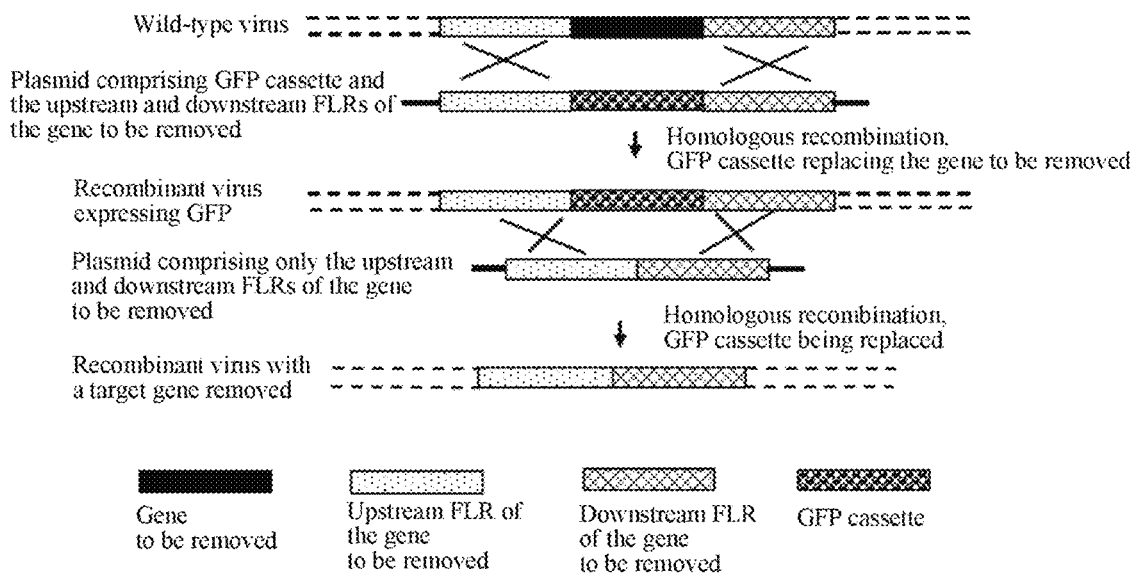
FIG. 5 is a schematic diagram of genetic recombination.
Figure 6:
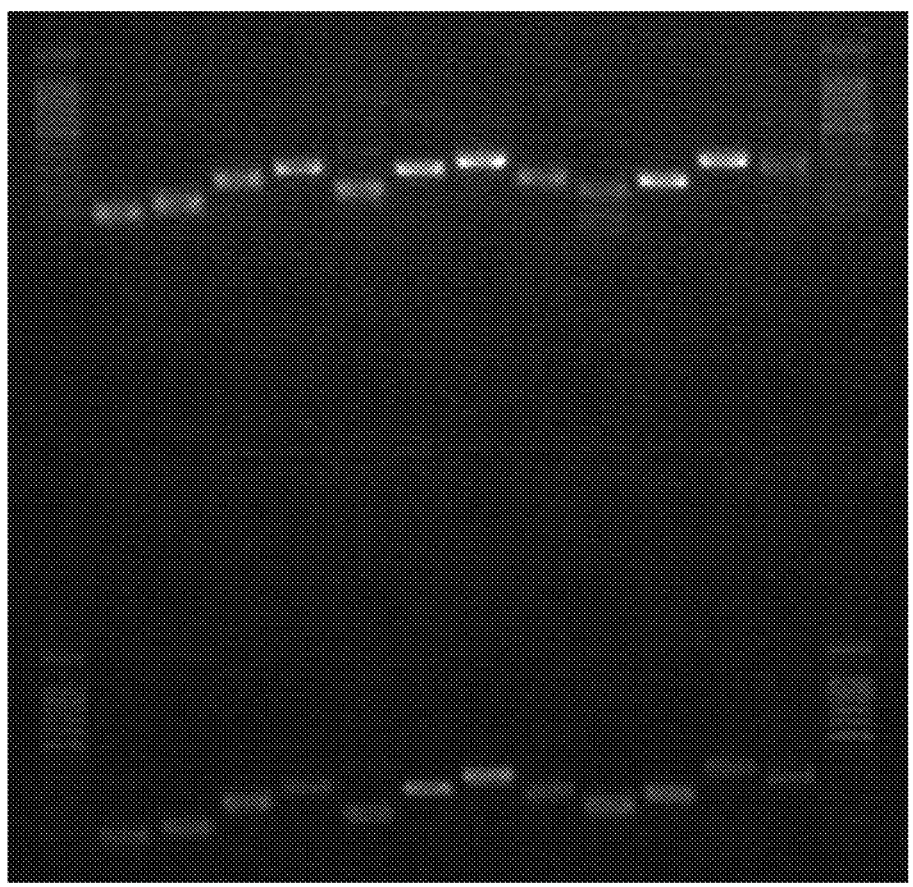
FIG. 6 illustrates an identification picture of gel electrophoresis of STR amplification.
Figure 7:
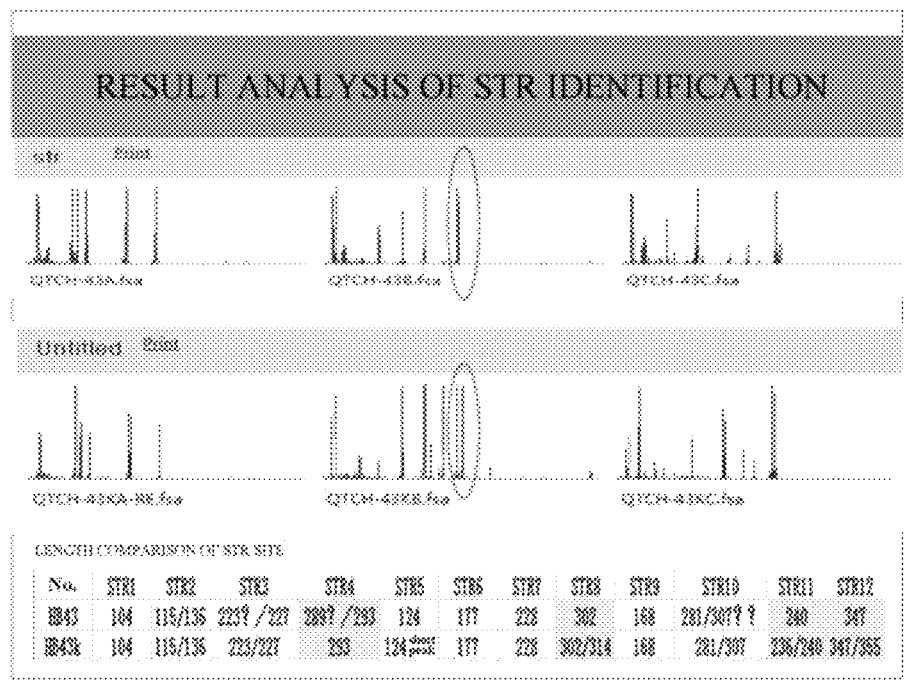
FIG. 7 illustrates a schematic diagram of STR sequencing analysis.
Figure 8A:
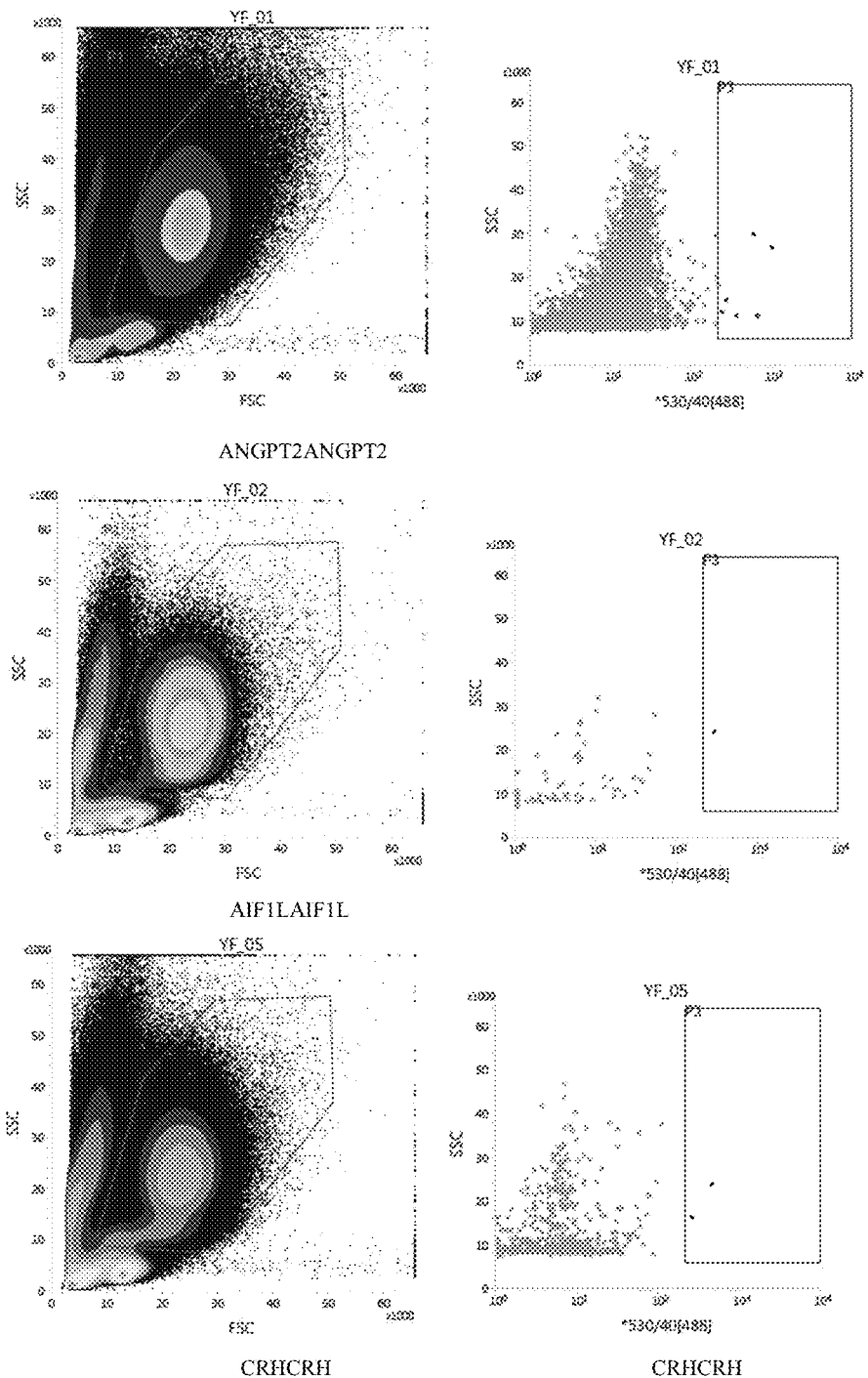
FIGS. 8a-8h illustrate flow cytometry results for the isolation of fetal cells using a kit of the present invention comprising a promoter sequence of the present invention.
Figure 8B:
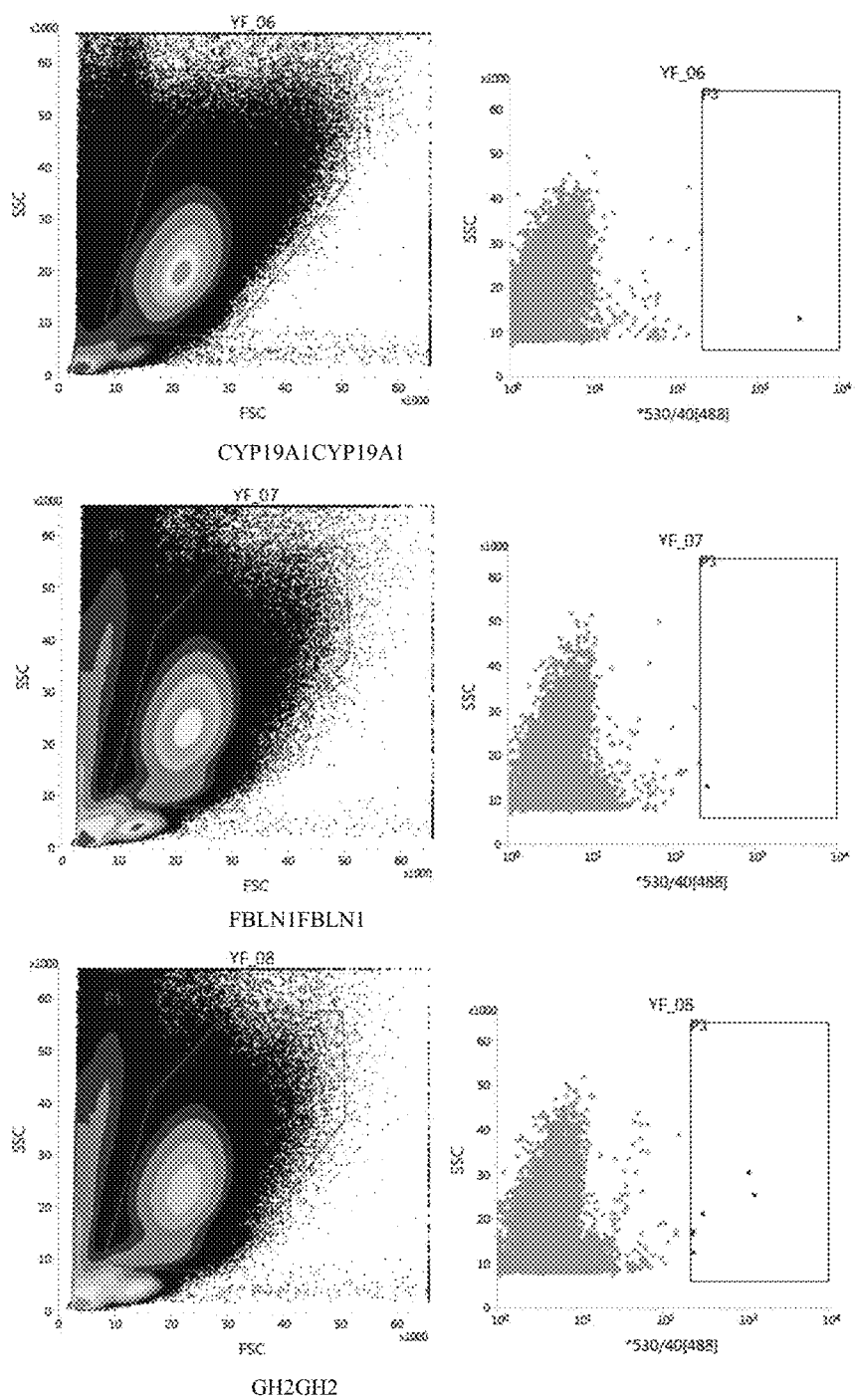
Figure 8C:
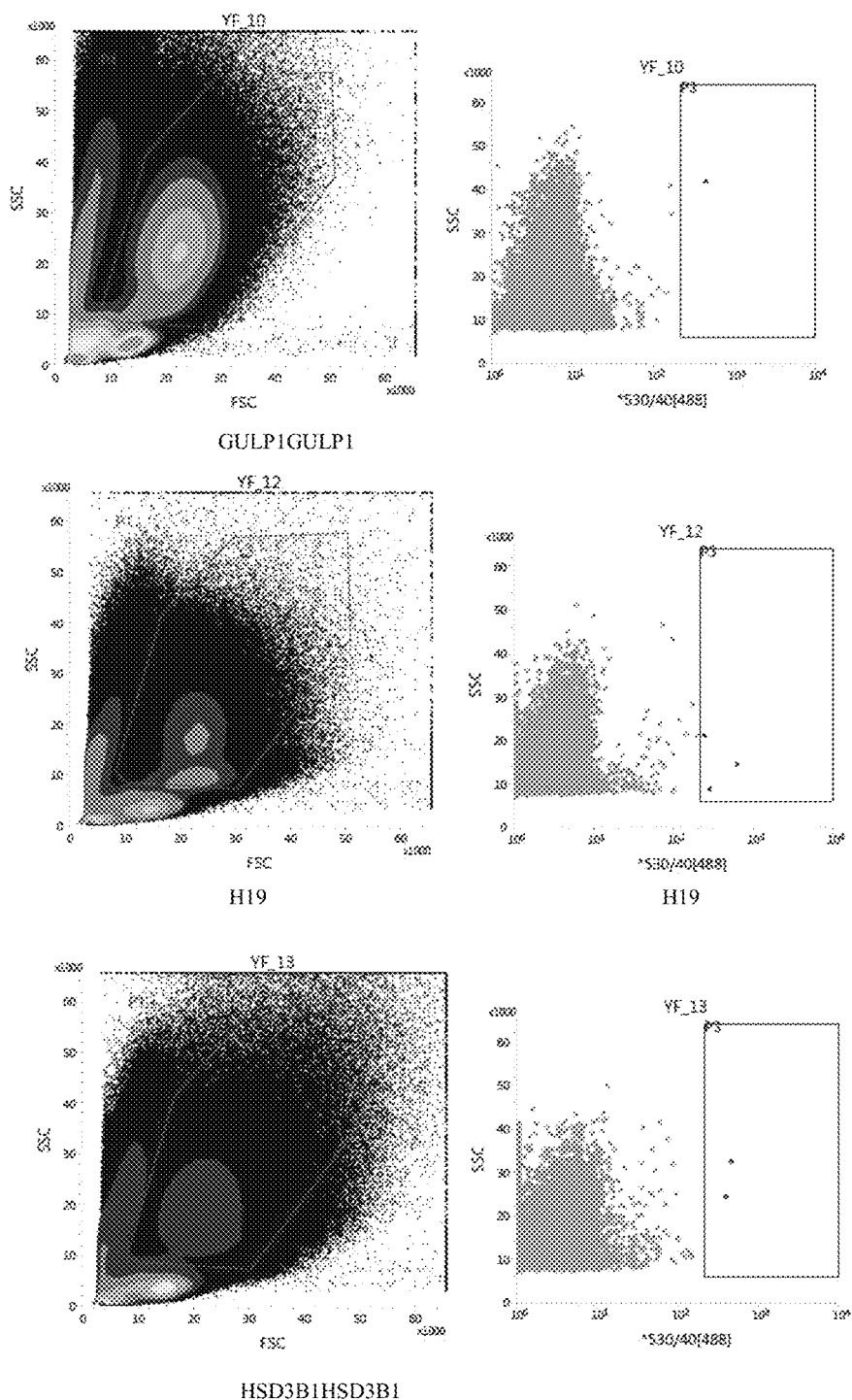
Figure 8D:
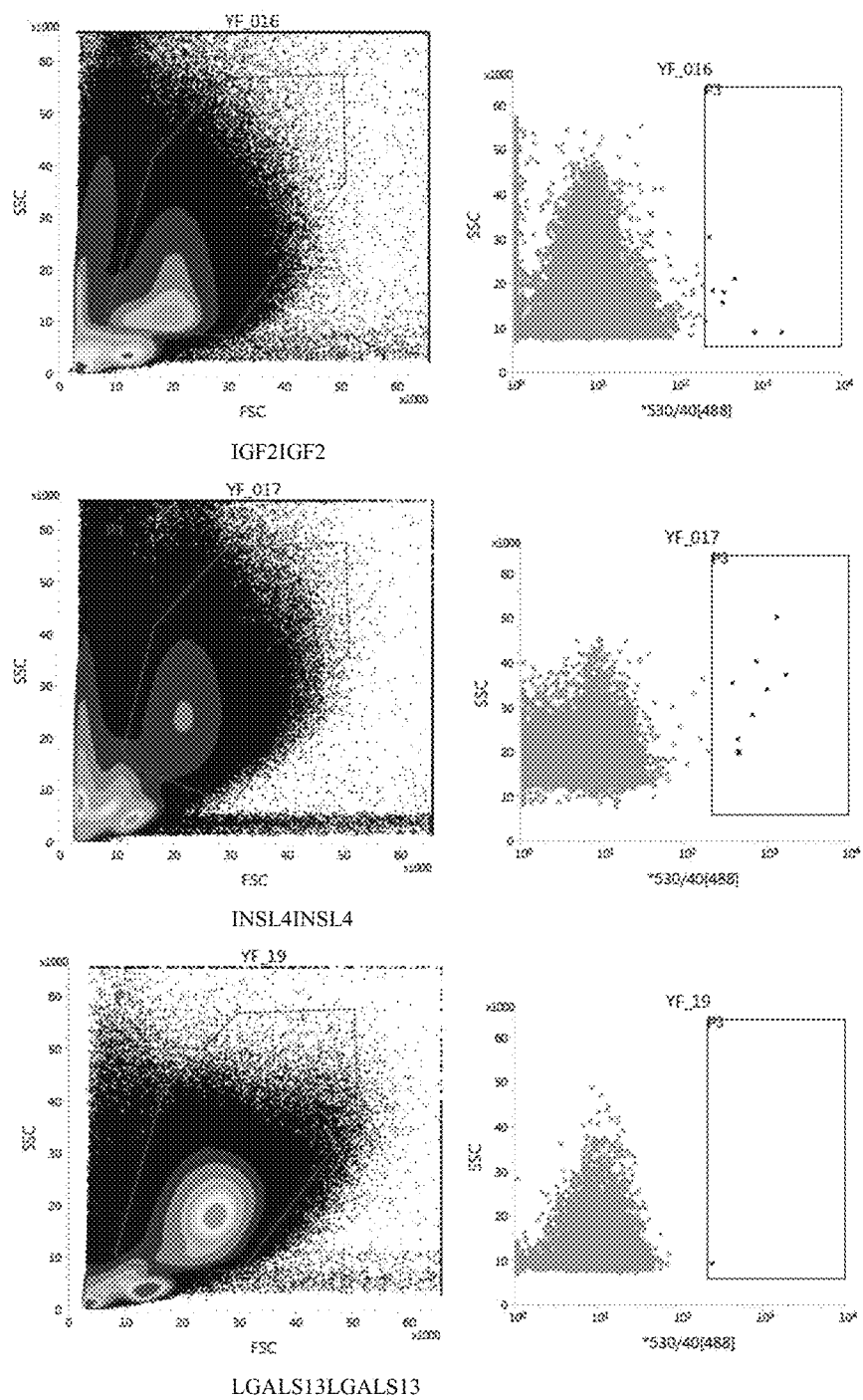
Figure 8E:
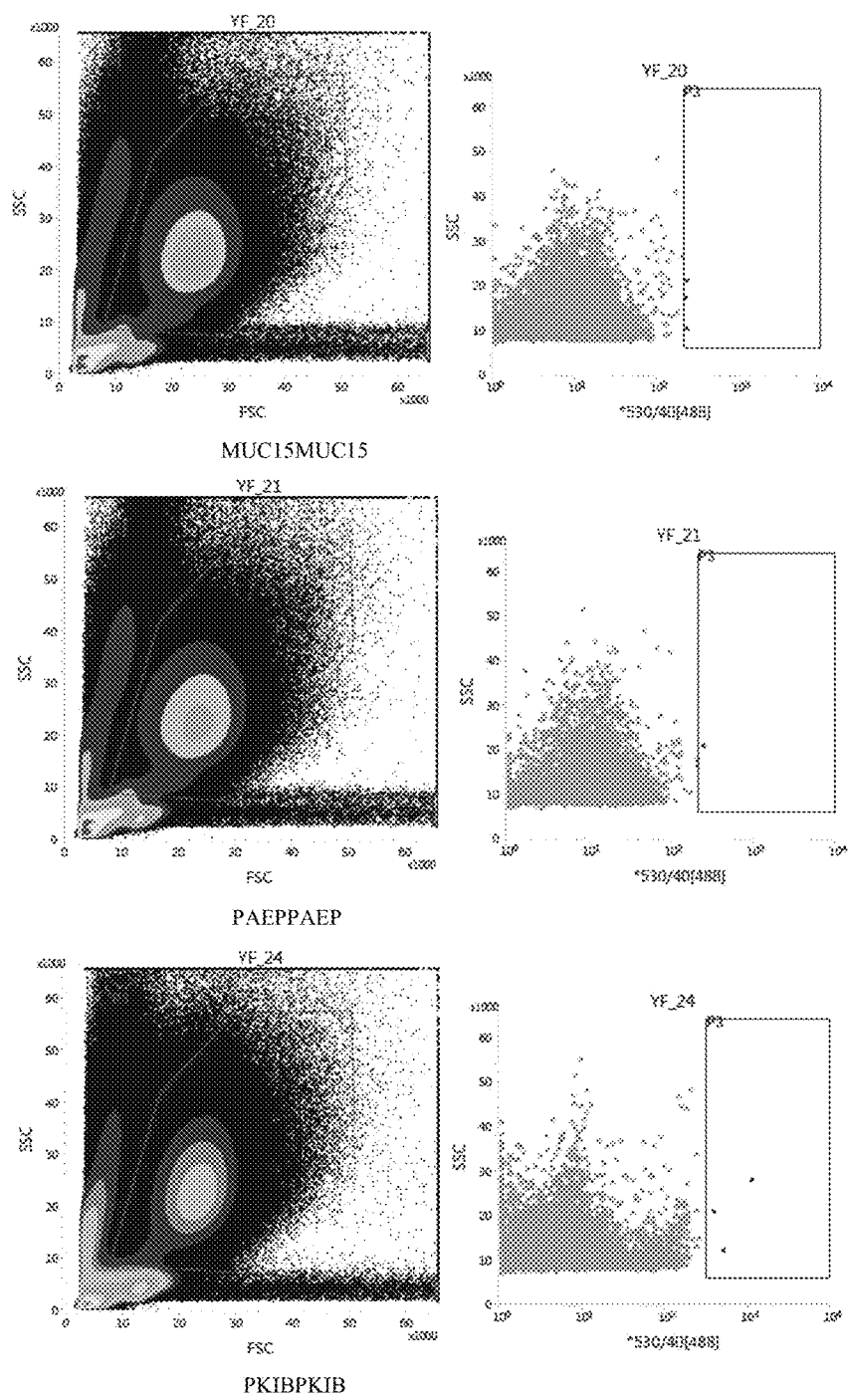
Figure 8F:
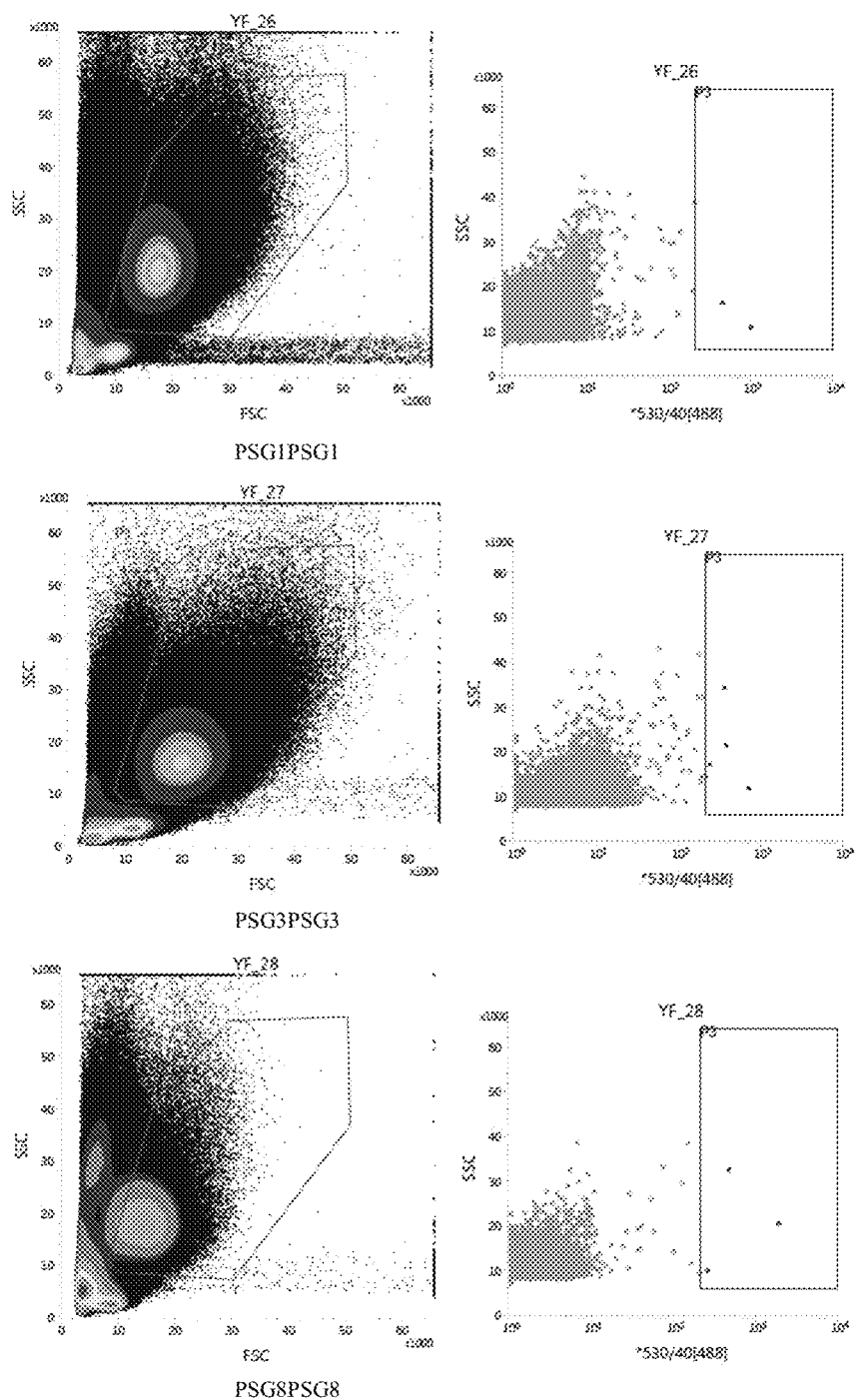
Figure 8G:
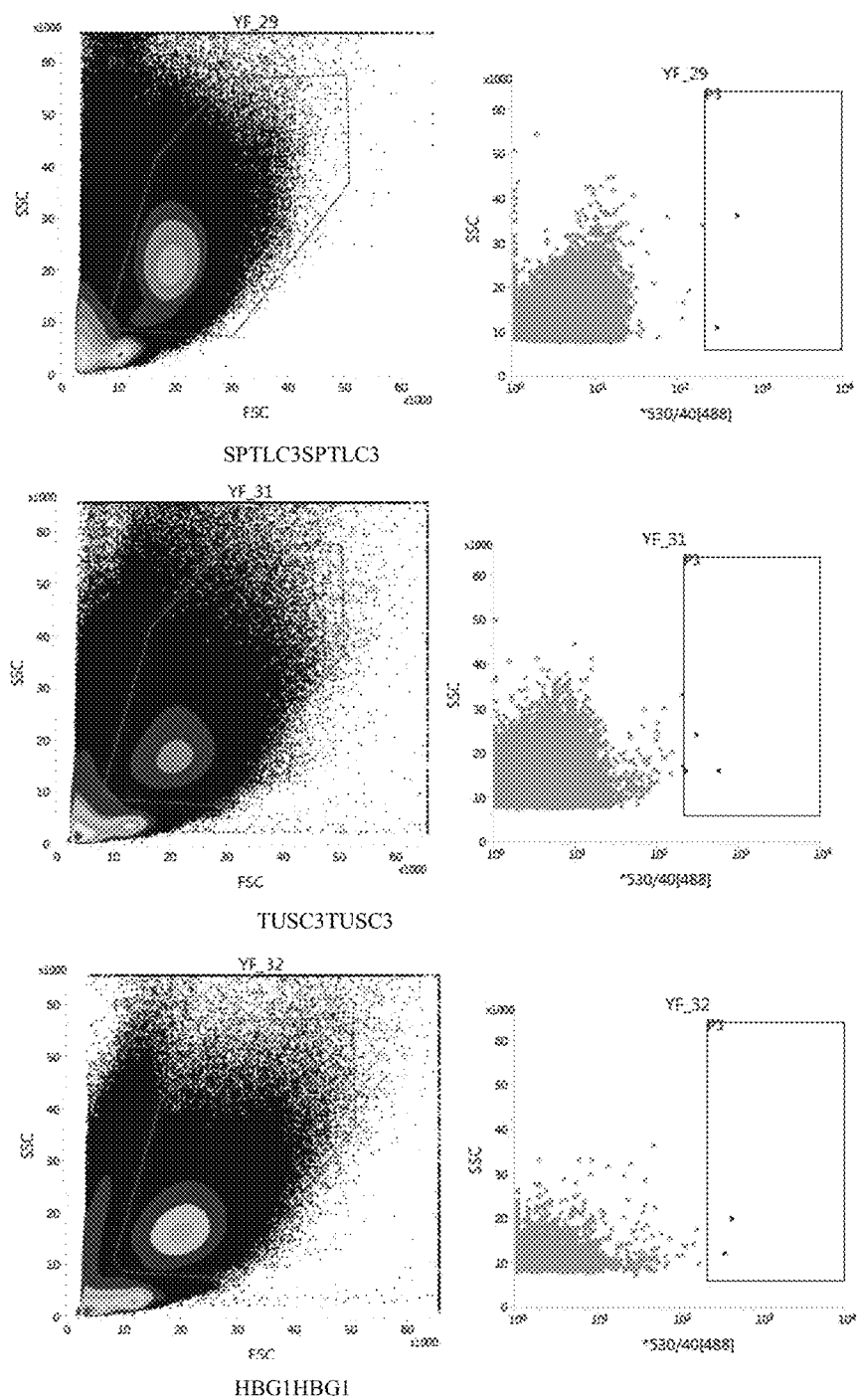
Figure 8H:
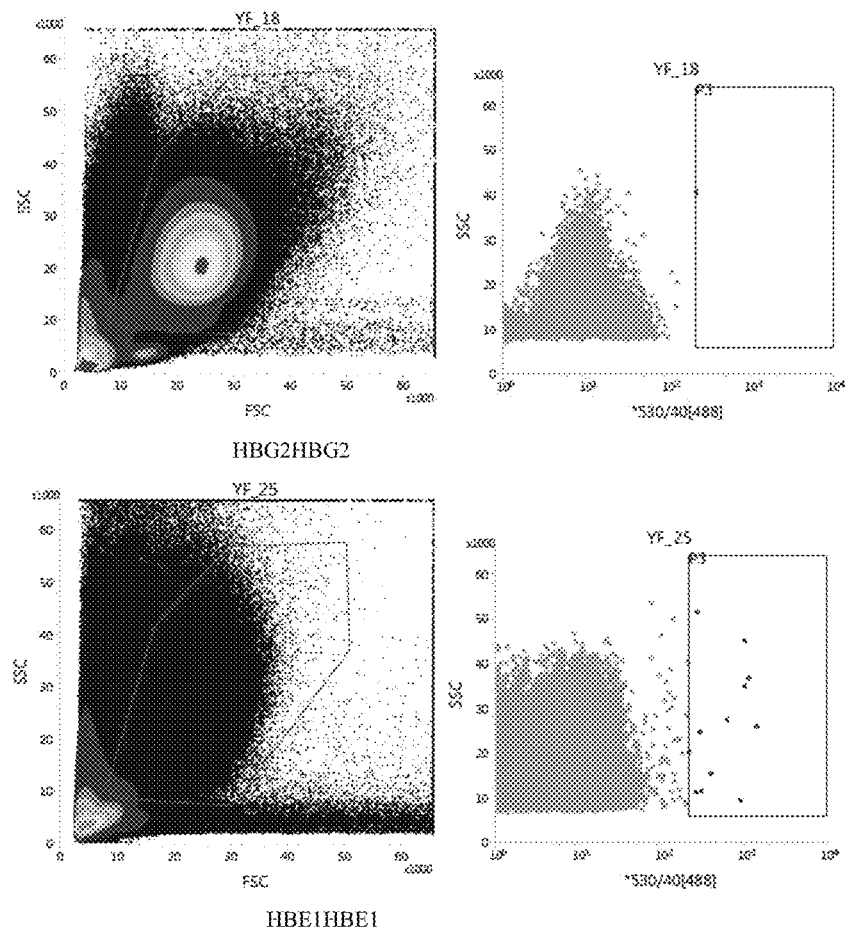

Material Sources:
1. Herpes simplex virus type I 17+(also known as herpes simplex virus type I 17) strain, which has a Latin name of Herpes Simplex Virus type I, is commercially available from the UK Health Protection Agency Culture Collections (HPA). The whole genome sequence of the herpes simplex virus type I 17+ is known (Genbank No. NC_001806).
2. Plasmid pSP37 was purchased from Promega; plasmid pcDNA3 was purchased from Invitrogen; and pcDNA3.1-eGFP was purchased from YRGENE.
3. As shown in FIG. 3, a BHK-ICP4 cell line was prepared by: (1) treating the pcDNA3-NHN-Np-ICP4 plasmid shown in FIG. 1 with EcoRI/XhoI to obtain an ICP4 gene expression cassette, and inserting the ICP4 gene expression cassette into an EcoRI/XhoI site of the pcDNA3 plasmid to obtain a pcDNA3-CMV-ICP4 plasmid; and (2) transfecting the BHK cells with the pcDNA3-CMV-ICP4 plasmid as obtained above to generate, by screening, a stable cell line BHK-ICP4.
4. All of the nucleotide sequences used in the present invention were synthesized by Shanghai Biotech.

Example 1

This example relates to the preparation of the recombinant herpes simplex virus type I of the present invention.
Purification of DNA of the Wild Type Herpes Simplex Virus Type I 17+ Virus
The wild type 17+ virus was grown with BHK cells, and the viral DNA of the wild type herpes simplex virus type I 17+ was purified using a DNAzol™ genomic DNA isolation kit (Helena Biosciences Cat. No. DN127200).
The BHK cells were grown in a 175 cm² culture flask, and the culture solution was DMEM containing 10% fetal bovine serum and 1% penicillin-streptomycin. The culture conditions were 37° C. and 5% carbon dioxide. When the cells grew to 90% confluency, the wild type herpes simplex virus type I 17+ virus was inoculated. Incubation continued for 24-48 hours, and when more than 90% of the cells showed cytopathy, the culture solution was removed and 10 ml of DNAzol was added. Pipetting was performed for 5 times with a 10 ml pipette, a cell lysing solution was transferred to a 50 ml Falcon tube, 5 ml of 100% ethanol was added, and the tube was gently shaken in an orbital motion to allow the viral DNA to fully precipitate. The DNA was picked into another tube with a pipette tip, washed with 70% ethanol and then picked into a small centrifuge tube with a pipette tip. The residual ethanol was removed by pipetting, and the DNA was dissolved in 1 ml of sterilized water, aliquoted and stored at −20° C. before use.
Construction of a pICP4del-eGFP Plasmid
Constructing a pICP4del-eGFP plasmid: inserting the ICP4 US FLR (ICP4 upstream repeat) fragment treated with SalI and the ICP4 DS FLR (ICP4 downstream repeat) fragment treated with SalI/HindIII into EcoRV/HindIII site of the pSP73 plasmid purchased from Promega to obtain a pICP4del plasmid; from the pcDNA3.1-eGFP plasmid, cleaving a CMV-eGFP fragment with EcoRI/XhoI, inserting the CMV-eGFP gene expression cassette into the EcoRV site of the pICP4del plasmid to obtain a pICP4del-eGFP plasmid.
Construction of a Recombinant Herpes Simplex Virus Type I with the ICP4 Gene Removed (oHSV1-d4GFP)
Preparing the required solutions and cells:
1) viral DNA of the wild type herpes simplex virus type I 17+, 1 mg/ml, prepared with a DNAzol kit (ibid);
2) pICP4del-eGFP plasmid, 1 mg/ml;
3) Hepes transfection buffer, 140 mM NaCl, 5 mM KCl, 0.75 mM $Na_2HPO_4$, 5.5 mM D-glucose, 20 mM Hepes, pH7.05;
4) 2M $CaCl_2$);
5) BHK cells grown at a confluency of 80-90% on a six-well culture plate;
6) 1.6% carboxymethyl cellulose (CMC), autoclaved at 121° C. for 20 minutes.
Procedures:
1) taking two sterile eppendorf tubes and adding 400 µl of Hepes transfection buffer to one of them;
2) adding, in the other eppendorf tube, 31 µl of 2M $CaCl_2$), 20 µl of wild type herpes simplex virus type I 17+ viral DNA and 8 µl of pICP4del-eGFP plasmid DNA, which were gently and homogenously mixed and slowly added to 400 µl of the Hepes transfection buffer by pipetting;
3) after gently and homogenously mixing them, allowing the resulting mixture to rest at room temperature for 40 minutes;
4) after the 40 minutes, removing the culture solution of BHK cells grown to 80-90% confluency in a six-well culture plate, and slowly adding the transfection buffer of the above step 2) to the culture plate, each well corresponding to one transfection mixture, followed by incubation in a 5% $CO_2$ and 37° C. incubator for 30 minutes;
5) after the 30 minutes, adding 1 ml of the cell culture solution into each well, and then putting the cell culture plate back into the 37° C. incubator for 5-hour incubation; 6) preparing a 20% DMSO solution with the Hepes buffer and placing the solution on ice;
7) after 5 hours, removing all the culture solution from the culture plate and washing the cells twice with 1 ml of a fresh culture solution;
8) adding 1 ml of the 20% DMSO solution to each well and leaving it at room temperature for 90 seconds;
9) removing the 20% DMSO solution quickly and carefully washing the cells twice with the fresh culture solution;
10) adding 2 ml of the fresh cell culture solution to each well, followed by incubation in a 37° C. and 5% $CO_2$ incubator, wherein viral plaques could be observed after 48 hours, the culture plates were frozen in a −70° C. refrigerator once, and after thawing, the cells and the culture solution were harvested; and
11) culturing BHK-ICP4 cells with a six-well culture plate, when the cells reached 70% confluency, removing the culture solution by pipetting and adding 1 ml of a serum-free culture solution to each well, then adding 0.1 or 10 µl of the harvest solution to each well and covering it with 2 ml of CMC (a complete culture solution (2:5)), after two days of growth, picking virus plaque with green fluorescence, which should be the 17+ recombinant virus (oHSV1-d4GFP) with the ICP4 gene removed, by a 20 µl pipette under a microscope, purifying the recombinant virus by 5 rounds of plaque selection, and then culturing the virus by the method described above to prepare and extract oHSV1-d4GFP virus genomic DNA.

Acquisition of a Promoter of a Gene Specifically Expressed in Fetal Trophoblast Cells (20 Specific Genes) or Nucleated Red Blood Cells (3 Specific Genes)

A list of fetus-specific genes was obtained by gene expression profile chips, and, specifically, the gene expression profiles of fetal cells and maternal cells were compared to screen for genes specifically expressed in the fetal cells. Screening was performed to acquire genes specifically expressed in the fetal trophoblast cells (20 specific genes) and genes specifically expressed in the fetal nucleated red blood cells (3 specific genes).

The promoter sequences of the specifically expressed genes were obtained by querying from the National Center for Biotechnology Information (NCBI) (see the attached table for the promoter sequences), two single-stranded DNAs of the positive-sense and antisense strands with NruI/HindIII sites were respectively obtained by base syntheses, and the single-stranded DNAs were annealed to form double-stranded DNA.

Annealing (50 µl reaction volume) system and reaction conditions:
50 µMol forward primer
50 µMol reverse primer
30 mM Tris-HCl (pH9.2)
95° C. for 5 minutes, 70° C. for 10 minutes, gradually cooling to room temperature.

The promoters thus obtained are shown in Table 3 below:

TABLE 3

| Promoter Name | Corresponding SEQ ID NO. | Promoter Source |
| --- | --- | --- |
| ANGPT2 | SEQ ID NO: 1 | trophoblast cell gene |
| AIF1L | SEQ ID NO: 2 | trophoblast cell gene |
| CRH | SEQ ID NO: 3 | trophoblast cell gene |
| CYP19A1 | SEQ ID NO: 4 | trophoblast cell gene |
| FBLN1 | SEQ ID NO: 5 | trophoblast cell gene |
| GH2 | SEQ ID NO: 6 | trophoblast cell gene |
| GULP1 | SEQ ID NO: 7 | trophoblast cell gene |
| H19 | SEQ ID NO: 8 | trophoblast cell gene |
| HSD3B1 | SEQ ID NO: 9 | trophoblast cell gene |
| IGF2 | SEQ ID NO: 10 | trophoblast cell gene |
| INSL4 | SEQ ID NO: 11 | trophoblast cell gene |
| LGALS13 | SEQ ID NO: 12 | trophoblast cell gene |
| MUC15 | SEQ ID NO: 13 | trophoblast cell gene |
| PAEP | SEQ ID NO: 14 | trophoblast cell gene |

TABLE 3-continued

| Promoter Name | Corresponding SEQ ID NO. | Promoter Source |
| --- | --- | --- |
| PKIB | SEQ ID NO: 15 | trophoblast cell gene |
| PSG1 | SEQ ID NO: 16 | trophoblast cell gene |
| PSG3 | SEQ ID NO: 17 | trophoblast cell gene |
| PSG8 | SEQ ID NO: 18 | trophoblast cell gene |
| SPTLC3 | SEQ ID NO: 19 | trophoblast cell gene |
| TUSC3 | SEQ ID NO: 20 | trophoblast cell gene |
| HBG1 | SEQ ID NO: 21 | nucleated red blood cell gene |
| HBG2 | SEQ ID NO: 22 | nucleated red blood cell gene |
| HBE1 | SEQ ID NO: 23 | nucleated red blood cell gene |

Construction of a Recombinant Herpes Simplex Virus Type I 17+NpICP4 with the ICP4 Gene Wild Type Promoter Replaced (1) PCR amplification of the ICP4 gene The DNA of the wild type herpes simplex virus type I 17+ virus was purified, and the ICP4 gene was amplified by three-stage PCR. The PCR primer sequences used are shown in Table 4 below:

TABLE 4

ICP4-1$^{st}$ Forward Primer 1 tttttttgaattc$^{147105}$atggcgtcggagaacaagcagcgcc$^{147129}$
Reverse Primer 2 $^{148279}$tggagccaccccatggcctccgcgt$^{148255}$ ICP4-2$^{nd}$ Forward Primer 3 $^{148205}$cgacgccgcgcagcagtacgccctg$^{148229}$
Reverse Primer 4 $^{149739}$cggcggggcgggcccggcgcaccg$^{149715}$ ICP4-3$^{rd}$ Forward Primer 5 $^{149675}$cctcatgtttgacccgcgggccctg$^{149699}$
Reverse Primer 6 ttttttctcgag$^{151001}$ttacagcacccgtcccctcgaac$^{150977}$ During PCR (50 µl reaction volume) amplifications of both upstream and downstream FLRs, the following reaction condition was used:
20 ng wild type viral DNA
30 mM Tris-HCl (pH 9.2)
10 mM magnesium sulfate
15 mM sodium chloride
100 µM dNTPs
50 µMol forward primer
50 µMol reverse primer
1 U (enzyme reaction unit) Taq DNA polymerase
Amplification was carried out for 35 cycles, and the temperature and duration of each cycle were: 95° C., 60 seconds; 62° C., 20 seconds; 72° C., 120 seconds.

The ICP4-1$^{st}$, ICP4-2$^{nd}$ and ICP4-3$^{rd}$ obtained by the above amplification were separately inserted into the EcoRV site of the pSP73 plasmid to obtain pSP73-ICP4-1$^{st}$, pSP73-ICP4-2$^{nd}$ and pSP73-ICP4-3$^{rd}$ plasmids, respectively.

(2) Construction of pICP4del-Np-ICP4 plasmids 1) inserting the double-stranded DNA of the promoter of the fetal trophoblast cell (20 specific genes)- or nucleated red blood cell (3 specific genes)-specifically expressed gene into NruI/HindIII site of the pcDNA3-NHN, respectively, to form a series of plasmids, collectively referred to as pcDNA3-NHN-Np;

2) treating the pSP73-ICP4-1$^{st}$ plasmid with EcoRI/BsrGI to obtain an ICP4-1$^{st}$ sequence, the pSP73-ICP4-2$^{nd}$ plasmid with BsrGI/PvuI to obtain an ICP4-2$^{nd}$ sequence and the pSP73-ICP4-3$^{rd}$ plasmid with PvuI/XhoI to obtain an ICP4-3$^{rd}$ sequence;

3) after linking the ICP4-1$^{st}$, ICP4-2$^{nd}$ and ICP4-3$^{rd}$ gene sequences obtained in step 2), inserting them into the EcoRI/XhoI site of the pcDNA3-NHN-Np plasmid, to obtain a pcDNA3-NHN-Np-ICP4 plasmid, in which the promoter of a fetal trophoblast cell-specifically expressed gene (20 specific genes) or the promoter of a fetal nucleated red blood cell-specifically expressed gene (3 specific genes) was separately linked to the ICP4 gene;

4) treating the pcDNA3-NHN-Np-ICP4 plasmid obtained in step 3) with PmeI/HpaI to obtain an Np-ICP4 gene expression cassette, and inserting the Np-ICP4 gene expression cassette into the SaII/BE site of the pICP4del plasmid to obtain a pICP4del-Np-ICP4 plasmid, wherein all plasmids were confirmed by sequencing analysis to avoid mutations.

(3) Preparation of BHK-ICP4 cells at 80-90% confluency with a six-well culture plate. The above oHSV1-d4GFP viral DNA and the pICP4del-Np-ICP4 plasmid DNA were co-transfected into the BHK-ICP4 cells. By homologous recombination, the oHSV1-d4GFP fluorescent protein expression cassette was homologously recombined with the ICP4 gene expression cassette linked to the promoter of a fetal trophoblast cell-specifically expressed gene (20 specific genes) or the promoter of a nucleated red blood cell-specifically expressed gene (3 specific genes), respectively, on the pcDNA3-NHN-Np-ICP4 plasmid, and plaque of the recombinant virus produced no fluorescence. The recombinant virus could be purified by selecting a plaque without green fluorescence. The recombinant virus (17+NpICP4) was cultured for proliferation to finally obtain a solution of $10^{10}$ pfu recombinant virus, and the solvent was a DMEM medium.

Construction of a Recombinant Herpes Simplex Virus Type I 17+NpICP4d34.5GFP with the ICP34.5 Gene Removed 1) Constructing plasmid pH2dI34.5-GFP containing an upstream flanking region sequence and a downstream flanking region sequence of the ICP34.5 gene The upstream and downstream flanking region sequences (Flanking Region, FLR for short) of the ICP34.5 gene were PCR-amplified by taking the full-length viral DNA obtained in step A as a template and using primers shown in Table 2. The PCR primer sequences used are shown in Table 5 below:

First, the PCR product of the upstream FLR was inserted into the PvuII/XbaI site of the pSP72 plasmid to obtain pSP72H2d34.5US. The PCR product of the downstream FLR was inserted into the EcoRV/BglII site of the pSP72H2d34.5US to obtain pH2d34.5 containing upstream and downstream flanking region sequences of the ICP34.5 gene. At last, the GFP expression cassette under the control of a CMV IE promoter was inserted into the EcoRV site of the pH2d34.5 to obtain pH2d34.5-GFP. All plasmids were confirmed by sequencing analysis to be free of mutations.

2) Constructing a recombinant herpes simplex virus type I 17+NpICP4d34.5GFP with the ICP34.5 gene removed BHK-ICP4 cells at 80-90% confluency were prepared using a six-well culture plate. The above 17+NpICP4 viral DNA and the pH2d34.5-GFP plasmid DNA were co-transfected into the BHK-ICP4 cells, and by homologous recombination, the GFP expression cassette replaced the ICP34.5 gene, and the plaque of the recombinant virus had a green fluorescence. After 5 rounds of plaque purification, the recombinant virus (17+NpICP4d34.5GFP) could be purified by selecting a green fluorescent plaque. The recombinant virus (17+NpICP4d34.5GFP) was cultured for proliferation to finally obtain a solution of $10^{10}$ pfu of recombinant virus, and the solvent was a DMEM medium.

The 23 viruses constructed are shown in Table 6 below:

| Promoter Name | Corresponding VirusName |
|---|---|
| ANGPT2 | ANGPT2p-HSVGFP |
| AIF1L | AIF1L p-HSVGFP |
| CRH | CRH p-HSVGFP |
| CYP19A1 | CYP19A1p-HSVGFP |
| FBLN1 | FBLN1p-HSVGFP |
| GH2 | GH2p-HSVGFP |
| GULP1 | GULP1p-HSVGFP |
| H19 | H19p-HSVGFP |
| HSD3B1 | HSD3B1p-HSVGFP |
| IGF2 | IGF2p-HSVGFP |
| INSL4 | INSL4p-HSVGFP |
| LGALS13 | LGALS13p-HSVGFP |
| MUC15 | MUC15p-HSVGFP |

TABLE 5

| Amplification of the upstream flanking region sequence of the ICP34.5 gene | Forward Primer | AAATCAGCTG$^{124356}$CGGTGAAGGTCGTCGTCAGAG$^{124376}$ |
|---|---|---|
| | Reverse Primer | AAATTCTAGA$^{125661}$GCCGGCTTCCCGGTATGGTAA$^{125641}$ |
| Amplification of the downstream flanking region sequence of the ICP34.5 gene | Forward Primer | AAATGATATC$^{126943}$CAGCCCGGGCCGTGTTGCGGG$^{126963}$ |
| | Reverse Primer | AAATAGATCT$^{127640}$CTCTGACCTGAGTGCAGGTTA$^{127620}$ |

During PCR (50 µl reaction volume) amplifications of both upstream and downstream FLRs, the following reaction condition was used:
- 20 ng wild type viral DNA
- 30 mM Tris-HCl (pH 9.2)
- 10 mM magnesium sulfate
- 15 mM sodium chloride
- 100 µM dNTPs
- 50 µMol forward primer
- 50 µMol reverse primer
- 1 U (enzyme reaction unit) Taq DNA polymerase Amplification was carried out for 35 cycles, and the temperature and duration of each cycle were: 95° C., 60 seconds; 62° C., 20 seconds; 72° C., 120 seconds.

-continued

| Promoter Name | Corresponding VirusName |
|---|---|
| PAEP | PAEP p-HSVGFP |
| PKIB | PKIB p-HSVGFP |
| PSG1 | PSG1p-HSVGFP |
| PSG3 | PSG3p-HSVGFP |
| PSG8 | PSG8p-HSVGFP |
| SPTLC3 | SPTLC3p-HSVGFP |
| TUSC3 | TUSC3p-HSVGFP |
| HBG1 | HBG1p-HSVGFP |
| HBG2 | HBG2p-HSVGFP |
| HBE1 | HBE1p-HSVGFP |

Example 2

This example describes a method for specifically capturing and isolating rare fetal cells.

The $10^{10}$ pfu recombinant virus solution prepared in Example 1 was centrifuged at 2000 rpm for 10 minutes, the supernatant DMEM culture medium was discarded, and the virus was suspended in an RPMI-1640 medium to obtain a virus suspension with a virus titer of $1\times10^7$ cfu.

The virus suspension having a virus titer of $1\times10^7$ cfu as prepared above was combined with a red blood cell lysing solution having a pH of 7 and a phosphate buffer having a pH of 7.3 to constitute the diagnostic kit for fetal cell capture and isolation as used in the following Examples 3 and 6, wherein the red blood cell lysing solution consisted of 0.15 M ammonium chloride, 10 nM potassium hydrogencarbonate and 1 nM ethylenediaminetetraacetic acid.

The virus suspension having a virus titer of $1\times10^7$ cfu as prepared above was combined with Ficoll-Urografin has a specific density of $1.077\pm0.001$ kg/m$^3$ and a phosphate buffer having a pH of 7.3 to constitute the kit for fetal cell capture and isolation as used in Example 4.

The virus suspension having a virus titer of $1\times10^7$ cfu as prepared above was separately assembled into the kit for fetal cell capture and isolation as used in Example 5.

Example 3

This example aims to describe the effectiveness and sensitivity of the diagnostic kit for fetal cell capture and isolation of the present invention.

Materials and Method:
1) taking 5 ml of peripheral blood from a pregnant women in 8 weeks of pregnancy with an EDTA anticoagulation tube, and adding 45 ml of a red blood cell lysing solution, followed by incubation at room temperature for 10 minutes;
2) after the red blood cells are lysed, performing centrifugation (800 g, 10 minutes);
3) removing the supernatant, and re-suspending a cell pellet in 10 ml of a phosphate buffer (PBS) with a pH of 7.3, followed by centrifugation (800 g, 10 minutes);
4) removing the supernatant, and re-suspending a cell pellet in 2 ml RPMI-1640;
5) mixing 2 ml of the cells obtained in step 4) with 0.1 ml of a suspension of the recombinant herpes simplex virus type I (PSG3 type) ($10^6$ Pfu/ml) of the present invention, and adding the resulting mixture to wells of a six-well culture plate;
6) incubating the culture plate in an incubator containing 5% $CO_2$ at 37° C.;
7) after 24 hours, collecting the cells, and pipetting the cells into a centrifuge tube, followed by centrifugation (500 g, 5 minutes);
8) discarding the supernatant, and adding 3 ml of PBS in each centrifuge tube for gently washing the cells, followed by centrifugation (500 g, 5 minutes);
9) removing the supernatant, re-suspending cell pellet in 0.4 ml of PBS, and adding 100 µl of APC-CD45 antibody (an APC-labeled antibody against leukocyte surface marker CD45), followed by incubation at room temperature for 30 minutes in the dark;
10) after the 30 minutes, gently washing each centrifuge tube with 4 ml of PBS, followed by centrifugation (500 g, 5 minutes);
11) after the centrifugation is completed, discarding the supernatant, adding PBS for re-suspending, and sorting CD45−/GFP+ cells by flow cytometry;
12) performing STR-identification on the cells obtained by sorting;
    (1) injecting the CD45−/GFP+ cells obtained by flow sorting into an EP tube containing 10 µL of a lysis buffer, and adding 1 µl of proteinase K to each EP tube, with an incubation in 56° C. water bath for 2 hours and in 80° C. water bath for 20 minutes, quickly placing on ice and instantaneously away from the EP tube:

preparing a pre-amplification mixture under an ultra-clean laminar flow cabinet based on the number (n) of reactions:
  pre-amplification buffer*: 20 µL×n
  pre-amplification enzyme*: 1.5 µL×n
  total: 21.5 µL×n preparing a pre-amplification buffer:
  10× ThermoPol buffer: 2 µL
  dNTPs (2.5 mM/each): 4 µL
  $MgSO_4$ (100 mM): 0.5 µL
  MA-G primer (15 µM): 1 µL
  MA-T primer (15 µM): 1 µL
  nucleic acid-free water: 11.5 µL
  usage amount: 20 µL/reaction pre-amplification enzyme:
  Bst DNA polymerase (8 U/µL): 0.8 µL
  Deep Vent (exo-)(2 U/µL): 0.7 µL
  usage amount: 1.5 µL/reaction (2) in the ultra-clean laminar flow cabinet, adding 20 µL of the pre-amplification mixture to each 10 µL of a cell lysis sample and transferring the mixture to a 200 µL PCR tube;
  (3) performing incubation in a PCR instrument;
  (4) preparing an amplification mixture outside the ultra-clean laminar flow cabinet based on the reaction number (n):
  amplification buffer*: 30 µL×n
  amplification enzyme*: 0.8 µL×n
  total: 30.8 µL×n preparing an amplification buffer:
  10× ThermoPol buffer: 3 µL
  dNTPs (2.5 mM/each): 4 µL
  $MgSO_4$ (100 mM): 1 µL
  MA primer (15 µM): 2 µL
  nucleic acid-free water: 20 µL
  usage amount: 30 µL/reaction amplification enzyme: Deep Vent (exo-) (2 U/µL)
  usage amount: 0.8 µL/reaction (5) taking out a pre-amplification product from the PCR instrument, briefly centrifuging the product, and adding 30 µL of an amplification mixture to each tube, followed by mixing homogenously;
  (6) performing incubation in the PCR instrument;
  (7) taking out an amplification product from the PCR instrument, briefly centrifuging the product, purifying the product with a PCR purification kit, and measuring the concentration of the product by Nanodrop;
13) performing individual identification of the amplified CFC genomic DNA:

At present, there are 12 short tandem repeat (STR) sites for individual identification. Taking the amplified CFC genomic DNA and the corresponding maternal genomic DNA as templates, 12 common PCR amplification reactions were carried out using primers of the 12 STR sites. Each reaction system was 20 µL, including 40-50 ng of the DNA template, 1 µL of the primer (10 mM), 2 µL of dNTPs (2.5 mM/each), and 0.1 µL of rTaq enzyme (5 U/µL). The STR genes and primer sequences are shown in Table 7 below:

TABLE 7

| Site | Labeled Primer | Fluorescence | Tube | Unlabeled Primer |
|---|---|---|---|---|
| CSF1PO | AACCTGAGTCTGCCAAGGACTAGC | 5'FAM | B | TTCCACACACCACTGGCCATCTTC |
| D13S317 | ACAGAAGTCTGGGATGTGGA | 5'FAM | B | GCCCAAAAGACAGACAGAA |
| D18S51 | GAGCCATGTTCATGCCACTG | 5'HEX | C | CAAACCCGACTACCAGCAAC |
| D16S539 | GTTTGTGTGTGCATCTGTAAGCATGTATC | 5'HEX | A | GGGGGTCTAAGAGCTTGTAAAAAG |
| D21S11 | TGTATTAGTCAATGTTCTCCAGAGAC | 5'FAM | A | ATATGTGAGTCAATTCCCCAAG |
| D5S818 | AGCCACAGTTTACAACATTTGTATCT | 5'FAM | A | GGTGATTTTCCTCTTTGGTATCC |
| D7S820 | ATGTTGGTCAGGCTGACTATG | 5'FAM | C | GATTCCACATTTATCCTCATTGAC |
| D8S1179 | ACCAAATTGTGTTCATGAGTATAGTTTC | 5'HEX | B | ATTGCAACTTATATGTATTTTTGTATTTCATG |
| FGA | GGCTGCAGGGCATAACATTA | 5'FAM | C | ATTCTATGACTTTGCGCTTCAGGA |
| TPOX | CGCTCAAACGTGAGGTTG | 5'FAM | B | GCACAGAACAGGCACTTAGG |
| THO1 | GTGATTCCCATTGGCCTGTTC | 5'FAM | C | ATTCCTGTGGGCTGAAAAGCTC |
| Amelogenin | CCCTGGGCTCTGTAAAGAATAGTG | 5'FAM | A | ATCAGAGCTTAAACTGGGAAGGTG |

The incubation conditions in the PCR instrument are shown in Table 8 below:

TABLE 8

| Number of Cycles | Temperature | Time |
|---|---|---|
| 1 | 94° C. | 2 minutes |
| 40 | 94° C. | 30 seconds |
|  | 60° C. | 30 minutes |
|  | 72° C. | 1 minute |
| 1 | 72° C. | 5 minutes |
| 1 | 4° C. | holding |

14) taking 5 μL of each amplification product for mixing, and sending the mixed amplification products to the sequencing company for gene sequencing, wherein the results are shown in Table 9 below:

TABLE 9

| Sample Number | AME | D5S | D21S | D16S | D13S | TPOX | CSF | D8S | THO1 | D7S | FGA | D18S |
|---|---|---|---|---|---|---|---|---|---|---|---|---|
| female parent 43 | 104 | 115/136 | 223/227 | 289/293 | 124 | 177 | 228 | 302 | 168 | 281/307 | 240 | 347 |
| CFC43k | 104 | 115/136 | 223/227 | 293 | 124 | 177 | 228 | 302/314 | 168 | 281/307 | 236/240 | 347/355 |
| female parent 44 | 104 | 136/140 | 223/227 | 281/288 | 124 | 172 | 224 | 306 | 168/176 | 232 | 281/285 | 343/355 |
| CFC44k | 104 | 136/140 | 223/227 | 282/289 | 124 | 172/178 | 223 | 282/306 | 168/176 | 232/240 | 282/285 | 340/352 |
| female parent 48 | 104 | 127/145 | 226/231 | 281/289 | 185/188 | 223/227 | 270/274 | 306/310 | 168/176 | 223/227 | 281/292 | 350/352 |
| CFC48k | 104 | — | 226/230 | 281 | 184/188 | — | 274 | 306 | 168/176 | 227 | 281/292 | 352 |

The results showed that the cells obtained by sorting had the same characteristic sequences as the mother's, and, meanwhile, also contained specific sequences different from the mother's, which proved that the obtained cells were fetal cells.

Example 4

1) Adding 10 ml of Ficoll-Urografin with a specific density of 1.077±0.001 kg/m³ in a 50 ml centrifuge tube;
2) taking 5 ml of heparin anti-coagulated venous blood for thorough and mixing homogenously with an equal volume of PBS having a pH value of 7.3, and slowly superimposing the resulting mixture along the tube wall on the stratified liquid surface by a dropper, with a clear interface remained, followed by horizontal centrifugation at 1000 g×20 minutes;
3) after the centrifugation, three layers existing within the tube, wherein the upper layer is serum and PBS solution, the lower layer is mainly red blood cells and granulocytes, and the middle layer is mononuclear cells (including lymphocytes, monocytes and tumor cells);
4) pipetting the mononuclear cell layer and placing in a new centrifuge tube, adding a 6-fold volume of PBS having a pH value of 7.3, centrifuging at 800 g×10 minutes, washing the cells twice with PBS, and then re-suspending the cells in 0.4 ml of RPMI1640;
5) mixing 2 ml of the cells obtained in step 4) with 0.1 ml of a recombinant herpes simplex virus type I (PSG3 type) suspension ($10^6$ Pfu/ml) of the present invention, and adding the resulting mixture to wells of a six-well culture plate;
6) incubating the culture plate in a 37° C. incubator containing 5% $CO_2$;
7) after 24 hours, collecting the cells, and pipetting the cells into a centrifuge tube, followed by centrifugation (500 g, 5 minutes);
8) discarding the supernatant, and adding 3 ml of PBS in each centrifuge tube for gently washing the cells, followed by centrifugation (500 g, 5 minutes);
9) removing the supernatant, re-suspending the cell pellet in 0.4 ml of PBS, and adding 100 μl of an APC-CD45 antibody (an APC-labeled antibody against leukocyte surface marker CD45), followed by incubation at room temperature for 30 minutes in the dark;
10) after 30 minutes, gently washing each centrifuge tube with 4 ml of PBS, followed by centrifugation (500 g, 5 minutes);

11) after the centrifugation is completed, discarding the supernatant, adding PBS for re-suspending, and sorting CD45−/GFP+ cells by flow cytometry;
12) performing STR-identification to the cells obtained by sorting (the same as steps 12-14 of Example 3).

The results are shown in Table 10 below:

TABLE 10

| Sample Number | AME | D5S | D21S | D16S | D13S | TPOX | CSF | D8S | THO1 | D7S | FGA | D18S |
|---|---|---|---|---|---|---|---|---|---|---|---|---|
| female parent 34 | 104 | 130/132 | 223/227 | 285/293 | 176/188 | 223/231 | 270 | 310/318 | 168 | 223/236 | 338/346 | 352 |
| CFC34K | 104 | 130 | 227 | 285/293 | 176 | 223 | 270/274 | 318 | 168 | — | 338 | 352 |
| female parent 35 | 104 | 127/132 | 223 | 287/300 | 185 | 219/223 | 278/281 | 314 | 175 | 227/236 | 281/285 | 342/370 |
| CFC35K | 104 | 132 | 223 | 227/285 | 185/188 | 223 | 270/278 | — | 175 | 236 | 285/296 | 370 |
| female parent 36 | 104 | 127/140 | 222 | 281/289 | 176/196 | 231/236 | 270/281 | 306/310 | 164/179 | 235 | 285/315 | 346/362 |
| CFC36K | 104 | 132/140 | 223/227 | 281 | 176 | — | 270/281 | 310 | 179 | 235/240 | 285/315 | 346 |

The results showed that the cells obtained by sorting had the same characteristic sequences as the mother's, and, meanwhile, also contained specific sequences different from the mother's, which proved that the obtained cells were fetal cells.

Example 5

1) dropping the cervical smear containing the cells on a glass slide in the middle;
2) mixing the cell suspension obtained in step 4) with 0.02 ml of the recombinant herpes simplex virus type I (PSG3 type) suspension ($10^6$ Pfu/ml) of the present invention;
3) incubating the culture plate in a 37° C. incubator containing 5% $CO_2$;
4) after 24 hours, detecting green fluorescent fetal cells with a fluorescence microscope;
5) collecting fluorescent cells, and performing STR-identification on the cells obtained by sorting;
6) performing STR-identification on the cells obtained by sorting (the same as steps 12-14 of Example 3).

The results are shown in Table 11 below:

TABLE 11

| Sample Number | AME | D5S | D21S | D16S | D13S | TPOX | CSF | D8S | THO1 | D7S | FGA | D18S |
|---|---|---|---|---|---|---|---|---|---|---|---|---|
| female parent 50 | 104 | 132/135 | 223/227 | 281/285 | 178/185/189 | 215/232 | 281 | 314/318 | 168/176 | 236 | 285/311 | 339/347 |
| CFC50k | 104 | 132/140 | 227/235 | 293 | 173 | 228/240 | 270 | 310/318 | 168/176 | 232/240 | 282/289 | 349/355 |
| HBGHL father | 104 | 132/135 | 223/227 | 281/285 | 178/189 | 215/232 | 281 | 314/318 | 168/176 | 236 | 285/311 | 339/347 |
| HBGHL mother | 104 | 132/140 | 227/235 | 293 | 173 | 228/240 | 270 | 310/318 | 168/176 | 232/240 | 282/289 | 349/355 |
| CFC | 104 | 132 | 223/227 | 293 | 173 | — | 270/281 | 310/318 | 168/176 | 232/236 | — | 349 |
| Sample Number | AME | D5S | D21S | D16S | D13S | TPOX | CSF | D8S | THO1 | D7S | FGA | D18S |

The results showed that the cells obtained by sorting had the same characteristic sequences as the mother's, and, meanwhile, also contained specific sequences different from the mother's, which proved that the obtained cells were fetal cells.

Example 6

The peripheral blood of a pregnant woman was treated as in Example 2, and the virus suspension having a virus titer of $1\times10^7$ cfu as prepared was combined with a red blood cell lysing solution having a pH of 7 and a phosphate buffer having a pH of 7.3 to constitute a diagnostic kit for fetal cell capture and isolation, wherein the red blood cell lysing solution consisted of 0.15 M ammonium chloride, 10 nM potassium hydrogencarbonate and 1 nM ethylenediaminetetraacetic acid. Fetal cell captures were performed with different viral vectors, respectively. The results are shown in FIGS. 8a-8h and Table 12 below:

TABLE 12

| Vector Virus Type (corresponding promoter name) | Result Description |
|---|---|
| ANGPT2p-HSVGFP | The blue dot in the P3 gate shows the captured fetal cells, the number of which is 6. |
| AIF1L p-HSVGFP | The blue dot in the P3 gate shows the captured fetal cell, the number of which is 1. |
| CRH p-HSVGFP | The blue dot in the P3 gate shows the captured fetal cells, the number of which is 2. |
| CYP19A1p-HSVGFP | The blue dot in the P3 gate shows the captured fetal cell, the number of which is 1. |

TABLE 12-continued

| Vector Virus Type (corresponding promoter name) | Result Description |
|---|---|
| FBLN1p-HSVGFP | The blue dot in the P3 gate shows the captured fetal cell, the number of which is 1. |
| GH2p-HSVGFP | The blue dot in the P3 gate shows the captured fetal cells, the number of which is 5. |
| GULP1p-HSVGFP | The blue dot in the P3 gate shows the captured fetal cell, the number of which is 1. |
| H19p-HSVGFP | The blue dot in the P3 gate shows the captured fetal cells, the number of which is 3. |
| HSD3B1p-HSVGFP | The blue dot in the P3 gate shows the captured fetal cells, the number of which is 2. |
| IGF2p-HSVGFP | The blue dot in the P3 gate shows the captured fetal cells, the number of which is 7. |
| INSL4p-HSVGFP | The blue dot in the P3 gate shows the captured fetal cells, the number of which is 8. |
| LGALS13p-HSVGFP | The blue dot in the P3 gate shows the captured fetal cell, the number of which is 1. |
| MUC15p-HSVGFP | The blue dot in the P3 gate shows the captured fetal cells, the number of which is 3. |
| PAEP p-HSVGFP | The blue dot in the P3 gate shows the captured fetal cell, the number of which is 1. |
| PKIB p-HSVGFP | The blue dot in the P3 gate shows the captured fetal cells, the number of which is 3. |
| PSG1p-HSVGFP | The blue dot in the P3 gate shows the captured fetal cells, the number of which is 2. |
| PSG3p-HSVGFP | The blue dot in the P3 gate shows the captured fetal cells, the number of which is 4. |
| PSG8p-HSVGFP | The blue dot in the P3 gate shows the captured fetal cells, the number of which is 3. |
| SPTLC3p-HSVGFP | The blue dot in the P3 gate shows the captured fetal cells, the number of which is 2. |
| TUSC3p-HSVGFP | The blue dot in the P3 gate shows the captured fetal cells, the number of which is 3. |
| HBG1p-HSVGFP | The blue dot in the P3 gate shows the captured fetal cells, the number of which is 2. |
| HBG2p-HSVGFP | The blue dot in the P3 gate shows the captured fetal cell, the number of which is 1. |
| HBE1p-HSVGFP | The blue dot in the P3 gate shows the captured fetal cells, the number of which is 12. |

As can be seen, the recombinant viruses constructed using the promoters of the present invention could all accomplish the purpose of capturing fetal cells.

---

The invention claimed is:

1. A recombinant herpes simplex virus type I, wherein the virus has a pathogenicity-related ICP34.5 gene fragment removed, has the ICP wild type promoter of the viral genome replaced with a promoter of a gene specifically expressed in fetal trophoblast cells or a gene specifically expressed in fetal nucleated red blood cells, and has a marker for tracing the recombinant herpes simplex virus type I inserted into the virus.

2. The recombinant herpes simplex virus type I according to claim 1, wherein the promoter of the gene specifically expressed in fetal trophoblast cells is a promoter selected from any one of SEQ ID NO: 1 to SEQ ID NO: 20, and the promoter of the gene specifically expressed in the fetal nucleated red blood cells is a promoter selected from any one of SEQ ID NO: 21 to SEQ ID NO: 23.

3. The recombinant herpes simplex virus type I according to claim 1, wherein the recombinant herpes simplex virus type I has a fluorescent protein expression cassette inserted at the position where the ICP34.5 gene is removed.

4. A diagnostic kit for prenatal screening during pregnancy, wherein the kit comprises is the recombinant herpes simplex virus type I according to claim 1.

\* \* \* \* \*